US006331609B1

(12) United States Patent
Lee et al.

(10) Patent No.: US 6,331,609 B1
(45) Date of Patent: Dec. 18, 2001

(54) PREPARATION OF HUMAN IGF VIA RECOMBINANT DNA TECHNOLOGY

(75) Inventors: James M. Lee, San Bruno, CA (US); Axel Ullrich, Munich (DE); Arjun Singh, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/464,361

(22) Filed: Jun. 5, 1995

Related U.S. Application Data

(63) Continuation of application No. 06/506,078, filed on Jun. 20, 1983, now abandoned, which is a continuation-in-part of application No. 06/501,353, filed on Jun. 6, 1983, now abandoned.

(51) Int. Cl.[7] .................................................. C07K 14/65
(52) U.S. Cl. ........................... 530/324; 530/350; 530/399; 435/69.7
(58) Field of Search ...................................... 530/350, 324, 530/399, 412; 435/69.7, 69.8

(56) References Cited

U.S. PATENT DOCUMENTS

| | | |
|---|---|---|
| 3,953,418 | 4/1976 | Yanaihara et al. . |
| 4,110,322 | 8/1978 | Green et al. . |
| 4,342,832 | 8/1982 | Goeddel et al. . |
| 4,350,764 | 9/1982 | Baxter et al. . |
| 4,366,246 | 12/1982 | Riggs . |
| 4,387,162 | 6/1983 | Aigle et al. . |
| 4,411,994 | 10/1983 | Gilbert et al. . |
| 4,425,437 | 1/1984 | Riggs . |
| 4,431,740 | 2/1984 | Bell et al. . |
| 4,440,859 | 4/1984 | Rutter et al. . |
| 4,530,904 | 7/1985 | Herschberger et al. . |
| 4,543,329 | 9/1985 | Daum et al. . |
| 4,546,082 | 10/1985 | Kurjan et al. . |
| 4,588,684 | 5/1986 | Brake . |
| 4,652,525 | 3/1987 | Rutter et al. . |
| 4,658,021 | 4/1987 | Goeddel et al. . |
| 4,745,179 | * 5/1988 | Ueda et al. ........................ 530/350 |
| 5,015,575 | 5/1991 | Brake et al. . |

FOREIGN PATENT DOCUMENTS

| | | |
|---|---|---|
| 1214739 | 12/1986 | (CA) . |
| 022242 | 7/1979 | (EP) . |
| 026598 | 4/1981 | (EP) . |
| 046039 | 2/1982 | (EP) . |
| 055945 | 7/1982 | (EP) . |
| 075444 | 3/1983 | (EP) . |
| 116201 | 8/1984 | (EP) . |
| 121352 | 10/1984 | (EP) . |
| 123228 | 10/1984 | (EP) . |
| 123289 | 10/1984 | (EP) . |
| 123294 | 10/1984 | (EP) . |
| 123544 | 10/1984 | (EP) . |
| 130166 | 1/1985 | (EP) . |
| 135094 | 3/1985 | (EP) . |
| 155655 | 9/1985 | (EP) . |
| 189481 | 8/1986 | (EP) . |
| 56-95199 | 8/1981 | (JP) . |
| 57-200343 | 12/1982 | (JP) . |
| 8302324 | 1/1985 | (NL) . |
| WO 84/03103 | 8/1984 | (WO) . |

OTHER PUBLICATIONS

Humbel, R., *Eur. J. Biochem.*, 190:445–462, 1990.*
Hammarberg, B. et al., *PNAS*, 86:4367–4371, 1989.*
Hammarberg, B. et al., *J. of Biotechnology*, 14:423–438, 1990.*
Rhee, H. J. et al., *J. of Biotechnology*, 13:293–304, 1990.*
Rinderknecht, E. et al., *FEBS Letters*, 89(2):283–286, 1978.*
Rinderknecht, E. et al., *J. Biol. Chem.*, 253(8):2769–76, 1978.*
Mullenbach, G. T. et al., *Fed. Proc.*, 42(7):abstract 434, 1983.*
Bishop, "Scientists Use Bacteria to Produce Insulin in Step Toward Better Care for Diabetics" *The Wall Street Journal* pp. 14 (Jun. 12, 1978).
Lacy et al., "Method for the Isolation of Intact Islets of Langerhans from the Rat Pancreas" *Diabetes* 16:35–39 (1967).
Nichol and Smith, "Amino–Acid Sequence of Human Insulin" *Nature* 181:483–485 (1960).
Steiner, "Concluding remarks" *Proinsulin, Insulin, C–Peptide*, Baba et al., Amsterdam–Oxford:Excerpta Medica pps. 449–452 (1979).
Ullrich et al., "The structure and expression of the insulin gene" *Proinsulin, Insulin, C–Peptide*, Baba et al., Amsterdam–Oxford:Excerpta Medica pp. 20–26 (1979).
Villa–Komaroff et al., "A bacterial clone synthesizing proinsulin" *Proc. Natl. Acad. Sci. USA* 75(8):3727–3731 (1978).
Weinstein, "A Generalized Homology Correlation for Various Hormones and Proteins" *Experientia* 28:1517–1522 (1972).
Yanaihara et al., "Syntheses of C–peptides and human proinsulin" *Diabetes* 27:149–160 (1978).
Horner and Hintz, "Further Comparisons of the [$^{125}$I] Somatomedin A and the [$^{125}$I ] Somatomedin C Radioreceptor Assays of Somatomedin Peptide" *J. Clin. Endocrinol. Metab.* 48(6):959–963 (1979).
Horner et al., "Comparison of [$^{125}$I] Somatomedin A and [$^{125}$I ] and Somatomedin C Radioreceptor Assays for Somatomedin Peptide Content in Whole and Acid–Chromatographed Plasma" *J. Clin. Endocrinol. Metab.* 47(6):1287–1294 (1978).

(List continued on next page.)

*Primary Examiner*—Marianne P. Allen
(74) *Attorney, Agent, or Firm*—Janet E. Hasak

(57) ABSTRACT

Human insulin-like growth factor is synthesized in recombinant cell culture by host cells transformed with expression vectors bearing DNA encoding human insulin-like growth factor.

1 Claim, 26 Drawing Sheets

OTHER PUBLICATIONS

Klapper et al., "Sequence Analysis of Somatomedin–C: Confirmation of Identity With Insulin–Like Growth Factor I" *Endocrinology* 112(6):2215–2217 (1983).

Svoboda et al., "Purification of Somatomedin–C from Human Plasma: Chemical and Biological Properties, Partial Sequence Analysis, and Relationship to Other Somatomedins" *Biochemistry* 19:790–797 (1980).

Chan et al., "Biosynthesis and Periplasmic Segregation of Human Proinsulin in *Escherichia coli*" *Proc. Natl. Acad. Sci. USA* 78(9):5401–5405 (1981).

"Chiron's elegant, general purpose, rDNA yeast system. A breakthrough?" *Biotech News* 3(10):1–3 (May 15, 1983).

"Har "byggdes" Sveriges forsta konstgjorda gen" *Sydsvenska Dagbladet* (Feb. 3, 1983).

"Konstgjort arvsanlag framstallt vid Kabi" *Goteborgs–Posten* (Feb. 3, 1983).

Achstetter and Wolf, "Hormone processing and membrane–bound proteinases in yeast" *The EMBO Journal* 4(1):173–177 (1985).

Alberts, B. *Molecular Biology of the Cell*, New York and London:Garland Publishing, Inc. pp. 215 (1983).

Astell et al, "The sequence of DNAs coding for the mating type loci of *saccharomyces cerevisiae*" *Cell* 27:15–23 (1981).

Baum, R. M., "Enzyme chemistry set to advance as new techniques are applied" *Chemical and Engineering News* pp. 7–14 (Jul. 14, 1986).

Bell et al., "Nucleotide sequence of a cDNA clone encoding human preproinsulin" *Nature* 282:525–527 (1979).

Bell et al., "Sequence of a cDNA clone encoding human preproinsulin–like growth factor II" *Nature* 310:775–777 (1984).

Bradshaw and Niall, "Insulin–related growth factors" *TIBS* 3:274–278 (1978).

Brake et al., "α–Factor–directed synthesis and secretion of mature foreign proteins in *Saccharomyces cerevisiae*" *Proc. Natl. Acad. Sci* 81:4642–4646 (1984).

Brake et al., "Identification and Characterization of a Structural Gene for the Yeast Peptide Mating Pheromone, a–factor" *J. Cell. Biochem.* (abstract 1497) Supp. 7B (Apr. 29, 1983).

Brousseau et al., "Synthesis of a human insulin gene V. Enzymatic assembly, cloning and characterization of the human proinsulin DNA" *Gene* 17:279–289 (1982).

Carpenter, "Epidermal growth factor is a major growth–promoting agent in human milk" *Chemical Abstracts* (abstract No. 215932m) 93:96 (1980).

Carpenter and Cohen, "Chapter 5—Epidermal Growth Factors" Biochemical Actions of Hormones (summarized in Chemical Abstracts, vol. 91 (11) 83626m (1979)), Academic Press, Inc. vol. V:203–247 (1978).

Carpenter et al., "Characterization of the binding of I–labeled epidermal growth factor to human fibroblasts" *J. Biol. Chemistry* 250(11):4297–4304 (Jun. 10, 1975).

Casadaban, "Transposition and Fusion of the lac Genes to Selected Promoters in *Escherichia coli* using Bacteriophage Lambda and Mu" *J. Mol. Biol.* 104:541–555 (1976).

Catanzaro et al., "Immunoscreening of Expression Clones Using Antibodies to Renin, EGF and NGF" *Manipulation and Expression of Genes in Eukaryotes,* Nagley et al. pp. 11–12 (1983).

Chan et al., "Cell–free synthesis of rat preproinsulins: Characterization and partial amino acid sequence determination" *Proc. Natl. Acad. Sci. USA* 73(6):1964–1968 (1976).

City of Hope; Genentech, Inc., "Research Scientists Synthesize Genes to "Command" Laboratory Bacteria to Manufacture Human Insulin" Press Release (Sep. 6, 1978).

Crea et al., "Chemical synthesis of genes for human insulin" *Proc. Natl. Acad. Sci. USA* 75:5765–5769 (1978).

Davis and Tai, "The mechanism of genes for human insulin" *Nature* 283:433–438 (1980).

Dayhoff, "Table of Contents, Preface, Data Section, Protein Data Introduction, Hormones, Active Peptides and Toxins" *Atlas of Protein Sequence and Structure,* Silver Spring:The National Biomedical Research Foundation vol. 5:vii–xxx, D1–D6, D176, D177, D2 (1972).

Dayhoff, "Table of Contents, Preface, Protein Data Introduction, Hormones and Active Peptides" *Atlas of Protein Sequence and Structure,* Silver Spring:The National Biomedical Research Foundation vol. 5(Supp. 3):vii–xxii, 25–28, 145–164 (1978).

Dayhoff, "Table of Contents, Preface, Protein Data Introduction, Hormones and Active Peptides" *Atlas of Protein Sequence and Structure,* Washington, DC:National Biomedical Research Foundation vol. 5(Supp. 2):vii–xx, 14, 21–24, 113–145 (1976).

deHaen et al., "Characterization of Proinsulin–Insulin Intermediates in Human Plasma" *J. Clin. Invest.* 62:727–737 (1978).

Dicker et al., "Similarities between fibroblast–derived growth factor and platelet–derived growth factor" *Chemical Abstracts* (abstract No. 201393r) 95:454 (1981).

Docherty et al., "Post–translational proteolysis in polypeptide hormone biosynthesis" *Annu Rev Physiol* 44:625–638 (1982).

Edge et al., "Total Synthesis of a Human Leukocyte Interferon Gene" *Nature* 292:756–762 (1981).

Estell et al., "Engineering an enzyme by site–directed mutagenesis to be resistant to chemical oxidation" *J. Biol. Chemistry* 260(11):6518–6521 (1985).

Frank and Chance, "Two Routes for Producing Human Insulin Utilizing Recombinant DNA Technology" *Munch. med. Wschr.* 125:14–20 (1983).

Gait, "Synthetic genes for human insulin" *Nature* 277:429–430 (1979).

Genentech, Inc., "First Successful Laboratory Production of Human Insulin Announced" Press Release (Sep. 6, 1978).

Gill et al. *Recombinant DNA,* Walton, A.G. pp. 213–227 (1981).

Goeddel et al., "Expression in *Escherichia coli* of Chemically Synthesized Genes for Human Insulin" *Proc. Natl. Acad. Sci. USA* 76(1):106–110 (1979).

Gregory, H., "Isolation and structure of urogastrone and its relationship to epidermal growth factor" *Nature* 257:325–327 (Sep. 25, 1975).

Grosjean and Fiers, "Preferential codon usage in prokaryotic genes: the optimal codon–anticodon interaction energy and the selective codon usage in efficiently expressed genes" *Gene* 18:199–209 (1982).

Higuchi et al., "A general method for cloning eukaryotic structural gene sequences" *Proc. Natl. Acad. Sci. USA* 73(9):3146–3150 (1976).

Hinnen et al., "High expression and secretion of foreign proteins in yeast" *Chemical Abstracts* (abstract No. 40931k) 102:150 (1985).

Hitzeman et al., "Expression of a Human Gene for Interferon in Yeast" *Nature* 293:717–722 (1981).
Hitzeman et al., "Secretion of human interferons by yeast" *Science* 219:620–625 (1983).
Hsiung et al., "Synthesis of human insulin gene. Part I. Development of reversed–phase chromatography in the modified triester method. Its application in the rapid and efficient synthesis of eight deoxyribooligonucleotides fragments constituting human insulin A DNA" *Nucl. Acids Res.* 6:1371–1385 (1979).
Hsiung et al., "Synthesis of human insulin gene. Part III. Chemical synthesis of 5'-phosphomonoester group containing deoxyribooligonucleotides by the modified phosphotriester method. Its application . . . seventeen fragments constituting human insulin C–chain DNA" *Nucl. Acids Res.* 8:5753–5765 (1980).
Humbel, "Insulin–like growth factors I and II" *European Journal of Biochemistry* 190:445–462 (1990).
Itakura et al., "Expression in *Escherichia coli* of a Chemically Synthesized Gene for the Hormone Somatostatin" *Science* 198:1056–1063 (1977).
Jansen et al., "Sequence of cDNA encoding human insulin-like growth factor I precursor" *Nature* 306:609–611 (1984).
Julius et al., "Isolation of the putative structural gene for the lysine arginine–cleaving endopeptidase required for processing of yeast prepro–Á–factor" *Cell* 37:1075–1089 (1984).
Kadonaga et al., "The role of the β–lactamase signal sequence in the secretion of proteins by *Escherichia coli*" *Journal of Biological Chemistry* 259(4):2149–2154 (1984).
Kemmler et al., "Studies on the Conversion of Proinsulin to Insulin" *Journal of Biological Chemistry* 246(22):6786–6791 (1971).
Keshet et al., "Cloning of bovine growth hormone gene and its expression in bacteria" *Nucleic Acids Research* 9:19–30 (1981).
Kurjan et al., "Structure of a yeast pheromone gene (MFα): a putative α–factor precursor contains four tandem copies of mature α–factor" *Cell* 30:933–943 (1982).
Li et al., "Total synthesis of insulin–like growth factor I (somatomedin C)" *Proc. Natl. Acad. Sci. USA* 80:2216–2220 (1983).
Lomedico et al., "Preparation of pancreatic mRNA: cellfree translation of an insulin–immunoreactive polypeptide" *Nucl. Acids Res.* 3(2):381–391 (1976).
Maniatis et al., "Expression of Eukaryotic Genes" *Molecular Cloning: A Laboratory Manual,* 1st edition, Cold Spring Harbor:Cold Spring Harbor Laboratory Press pp. 412–413 (1982).
Maniatis et al., "Preface, Contents, and List of References" *Molecular Cloning: A Laboratory Manual,* 1st edition, Cold Spring Harbor:Cold Spring Harbor Laboratory Press pp. iii–x; 507–520 (1983).
Mercereau–Puijalon et al. *Expression of Eukaryotic Viral & Cellular Genes,* Pettersson et al. pp. 295–303 (1981).
Mercereau–Puijalon et al., "Synthesis of a Chicken Ovalbumin–like Protein in the Yeast *Saccharomyces cerevisiae*" *Gene* 11:163–167 (1980).
Merryweather et al. *Federation Proceedings* (AB#1161) 42(7):1956 (May 1, 1983).
Miller et al., "Synthesis of Biologically Active Proteins by Recombinant DNA Technology" *Drug Development Research* 1:435–454 (1981).

Mizuno and Matsuo, "A novel protease from yeast with specificity towards paired basic residues" *Nature* 309:558–560 (1984).
Mullenbach et al. Amer. Soc. Biol. Chemists, 74th Annual Meeting, San Francisco, CA (Poster Jun. 5, 1983).
Mullenbach et al., "The Chemical Synthesis, Molecular Cloning and Expression in Yeast of Genes Coding for Human Insulin–Like Growth Factors" *Federation Proceedings* (AB#434) 42(7):1832 (May 1, 1983).
Narang et al., "Synthesis of the human insulin gene. Part IV. New synthetic deoxyribooligonucleotide adaptors and primter for DNA cloning and sequence analysis" *Nucl. Acids Res. Symp Series.* 7:377–385 (1980).
O'Farrell et al., "Regulated Expression by Readthrough Translation from a Plasmid–Encoded beta–Galactosidase" *J. Bacteriology* 134(2):645–654 (1978).
Ohsuye et al., "Expression of chemically synthesized α–neo–endorphin gene fused to *E. coli* alkaline phosphatase" *Nucl. Acids Res.* 11(5):1283–1295 (1983).
Oyer et al., "Studies on Human Proinsulin" *Journal of Biological Chemistry* 246(5):1375–1386 (1971).
Polisky et al., "A plasmid cloning vehicle allowing regulated expression of eukaryotic DNA in bacteria" *Proc. Natl. Acad. Sci. USA* 73:3900–3904 (1976).
Riggs et al., "Synthesis, Cloning, and Expression of Hormone Genes in *Escherichia coli*" *Recent Prog. in Hormone Res.* 16:261–274 (1980).
Rinderknecht and Humbel, "The amino acid sequence of human insulin–like growth factor I and its structural homology with proinsulin" *Journal of Biological Chemistry* 253(8):2769–2776 (1978).
Rinderknecht and Humbel, "Amino–terminal sequences of two polypeptides from human serum with nonsuppressible insulin–like and cell–growth–promoting activities: Evidence for structural homology with insulin B chain" *Proc. Natl. Acad. Sci. USA* 73(12):4379–4381 (1976).
Rinderknecht and Humbel, "Polypeptides with nonsuppressible insulin–like and cell–growth promoting activities in human serum: isolation, chemical characterization, and some biological properties of forms I and II" *Proc. Natl. Acad. Sci. USA* 73(7):2365–2369 (1976).
Rinderknecht et al., "Primary structure of human insulin-like growth factor II" *FEBS Letters* 89(2):283–286 (1978).
Roberts, T., "A lac Promoter System for the Overexpression of Prokaryotic and Eukaryotic Genes in *E. coli*" *Promoters: Structure and Function,* Rodriguez et al. (eds.), Praeger Scientific pp. 454–461 (1982).
Rossi et al., "An Alternate Method for Synthesis of Double–stranded DNA Segments" *Journal of Biological Chemistry* 257(16):9226–9229 (1982).
Rutter, "Production of "Valuable" Proteins in Alternate Biological Hosts" *Recombinant DNA and Genetic Experimentation,* Morgan and Whelan, Oxford:Pergamon Press pp. 123–128 (1979).
Schoenle et al., "Insulin–like growth factor I stimulates growth in hypophysectomized rats" *Nature* 296:252–253 (1982).
Server and Shooter, "Nerve Growth Factor" *Adv. Protein Chem.* 31:339–409 (1977).
Shine et al., "Expression of cloned β–endorphin gene sequences by *Escherichia coli*" *Nature* 285:456–461 (1980).
Stebbing, "Activity of cloned gene products in animal systems" *Miami Winter Symposia* 19:445–447 (1982).

Steiner, "Insulin Today" *Diabetes* 26:322–340 (1977).

Steiner et al., "Discussion of Jackson & Blobel: canine pancreatic signal peptidase" *Annals of the NY Acad. Sci.* 343(1):403–404 (1980).

Steiner et al.,"Insulin Biosynthesis: Evidence for a Precursor" *Science* 157:697–700 (1967).

Steiner et al., "New aspects of insulin biosynthesis" pp. 9–19 (1979).

Suggs et al., "Use of Synthetic Oligonucleotides as Hybridization Probes: Isolation of Cloned cDNA Sequences for Human $\beta_2$ Microglobulin" *Proc. Natl. Acad. Sci. USA* 78(11):6613–6617 (Nov. 1991).

Sung et al., "Synthesis of the human insulin gene. Part II. Further Improvements in the modified phosphotriester method and the synthesis of seventeen deoxyribooligonucleotide fragments constituting human insulin chains B and mino–C DNA" *Nucl. Acids Res.* 7:2199–2212 (1979).

Sures et al., "Nucleotide sequence of human preproinsulin complementary DNA" *Science* 208:57–59 (1980).

Tacon et al., "The construction and characterization of plasmid vectors suitable for the expression of all DNA phases under the control of the *E. coli* tryptophan promoter" *Molecular & General Genetics* 177(3):427–438 (1980).

Talmadge et al., "Eukaryotic Signal Sequence Transports Insulin Antigen in *Escherichia coli*" *Proc. Natl. Acad. Sci. USA* 77(6):3369–3373 (1980).

Taniguchi et al., "Expression of the Human Fibroblast Interferon Gene in *Escherichia coli*" *Proc. Natl. Acad. Sci. USA* 77(9):5230–5233 (1980).

Taniguchi et al., "Structure and expression of a cloned cDNA for human interleukin–2" *Nature* 302(24):305–309 (1983).

Taylor et al., "Epidermal Growth Factor" *J. Biol. Chemistry* 247:5928–5934 (1972).

Ullrich et al., "A bacterial clone synthesizing proinsulin" *Proc. Natl. Acad. Sci. USA* 75(8):3727–3731 (1978).

Ullrich et al., "Rat insulin genes: construction of plasmids containing the coding sequences" *Science* 196:1313–1319 (1977).

Valenzuela et al., "Is sequence conservation in interferons due to selection for functional proteins?" *Nature* 313:698–700 (Feb. 1985).

Wells and Powers, "In vivo formation and stability of engineered disulfide bonds in subtilisin" *J. Biol. Chemistry* 261(14):6564–6570 (May 15, 1986).

Wetzel et al., "Expression in *escherichia coli* of a chemically synthesized gene for a "mini–C" analog of human proinsulin" *Gene* 16:63–71 (1981).

Williams et al., "Cytoplasmic inclusion bodies in *escherichia coli* producing biosynthetic human insulin proteins" *Science* 215:687–689 (1982).

Woods et al., "Isolation of cDNA clones for the human complement protein factor B, a Class III Major Histocompatibility Complex Gene Product." *Proc. Natl. Acad. Sci. USA* 79:5661–5665 (Sep. 1982).

Wunsch et al., "Studies on Enzymatic Methods for Processing Hybrid Proteins Produced by Recombinant DNA Technology" *Hoppe–Seyler's Z. Physiol. Chem.* 362:1285–1287 (1981).

Zapf and Froesch, "Radioimmunological determination of insulinlike growth factors I and II in normal subjects and in patients with growth disorders and extrapancreatic tumor hypoglycemia" *Chemical Abstracts* (abstract No. 218639y) 95:385 (1981).

Zapf et al., "Insulin–like growth factors I and II: some biological actions and receptor binding characteristics of two purified constituents of nonsuppressible insulin–like activity of human serum" *Chemical Abstracts* (abstract No. 140765r) 89:78 (1978).

\* cited by examiner

Fig. 1.

Chemically Synthesized DNA - IGF-1

IGF-1 LEFT HALF 1L (43-mer)
AGTTCTGATTTCGAATTCTATGGGTCCGGAAACTCTGTGCGGC 3L (43-mer)
GACACGCCGCGACTCGACCAACTGCGAGACGTCTTAGTCTTGA 2L (46-mer)
AGTTCTGATTCTGCAGTTCGTATGTGGTGATCGAGGCTTCTACTTC 4L (46-mer)
GAAGATGAAGTTGTTTGGCTGACCCATGCCTAGGAGTTAGTCTTGA

IGF-1 RIGHT HALF 1R (46-mer)
GACTGACTTCTGGATCCTCCTCTCGTCGTGCTCCGCAAACCGGCAT 3R (46-mer)
TTGGCCGTAGCAACTACTTACGACAAAAGCCAGGACATTCAGTCAG 2R (54-mer)
TGACTGACTTGGTCCTGTGACCTTCGCCGTCTGGAAATGTACTGCGCTCCGCTG 4R (46-mer)
CGAGGCGACTTTGGCCGATTCAGACGTATCAGCTGAGTTCAGTCAG

Fig. 2.

DNA Polymerase I Synthesized Double Stranded DNAs

IGF-1 LEFT HALF

Part 1

12 additional bases

```
                    1  2  3  4  5  6  7  8  9 10 11 12 13 14 15           9 additional bases
                   IniGlyProGluThrLeuCysGlyAlaGlyGluValAspAlaLeuGln
         AGTTCTGAATTCTATGGGTCCGGAAACTCTGTGCGGCGCTGGTTGACGCTCTGCAGAATCAGAACT
         TCAAGACTAAAGATTAAGATACCCAGGCCTTTGAGACACGCCGCGACCAACTGCGAGACGTCTTAGTCTTGA
              EcoRI                                          PstI
```

Part 2

11 additional bases

```
      15 16 17 18 19 20 21 22 23 24 25 26 27 28 29 30 31 32              12 additional bases
     GlnPheValCysGlyAspArgGlyPheTyrPheAsnLysProThrGlyTyrGly
  AGTTCTGATTCTGCAGTTCGTATGTGGTATCGAGGCTTCTACTTCAACAAACCGACTGGGTACGACTCCTCAATCAGAACT
  TCAAGACTAAGACGTCAAGCATACACCACTAGCTCCGAAGATGAAGTTGTTTGGCTGACCATGCTAGGAGTTAGTCTTGA
       PstI                                                    BamHI
```

Part 3

11 additional bases

```
                33 34 35 36 37 38 39 40 41 42 43 44 45 46 47 48 49 50 51      12 additional bases
               SerSerSerArgArgAlaProGlnThrGlyIleValAspGluCysCysPheArgSer
         GACTGACTTCTGGATCCTCCTCTCGTCGTGCTCCGCAAACCGGCATCGTTGATGAATGTTGTTTTCGGTCCTGTAAGTCAGTC
         CTGACTGAAGACTAGGAGGAGACGAGCAGCACGAGGCGTTTGGCCGTAGCAACTACTTACGACAACAAAAGCCAGGACATTCAGTCAG
              BamHI                                                        AvaII
```

Part 4

10 additional bases

```
        51 52 53 54 55 56 57 58 59 60 61 62 63 64 65 66 67 68 69 70           11 additional bases
       SerCysAspLeuArgArgLeuGluMetTyrCysAlaProLeuLysProAlaLysSerAlaTer
  TGACTGACTTGGTCCTGTGACCTTCGCCGTCTGGAAATGTACTGCGCTCCGCTGAAACCGGCTAAGTCTGCATAGTCGACTCAAGTCAGTC
  ACTGACTGAACCAGGACACTGGAAGCGGCAGACCCTTTACATGACGCGAGGCGACTTTGGCCGATTCAGACGTATCAGCTGAGTTCAGTCAG
       AvaII                                                                Sall
```

IGF-1 RIGHT HALF

IGF-1 LEFT HALF

Part 1

```
          1   2   3   4   5   6   7   8   9  10  11  12  13  14  15
         Ini Gly Pro Glu Thr Leu Cys Gly Ala Glu Leu Val Asp Ala Leu Gln
     AATTCTATGGGTCCGGAAACTCTGTGCGGCGCTGAGCTGGTTGACGCTCTGCAG
         GATACCCAGGCCTTTGAGACACGCCGCGACTCGACCAACTGCGAGA
         EcoRI                                           PstI
```

Part 2

```
         16  17  18  19  20  21  22  23  24  25  26  27  28  29  30  31
         Phe Val Cys Gly Asp Arg Gly Phe Tyr Phe Asn Lys Pro Thr Gly Tyr
     TTCGTATGTGGTGATCGAGGCTTCTACTTCAACAAACCGACTGGGTAC
     CGTCAAGCATACACCACTAGCTCCGAAGATGAAGTTGTTTGGCTGACCATGCCTAG
     PstI                                                BamHI
```

Fig. 3.

IGF-1 RIGHT HALF

```
          33 34 35 36 37 38 39 40 41 42 43 44 45 46 47 48 49 50 51
          SerSerArgArgAlaProGlnThrGlyIleValAspGluCysPheArgSer
       GACTGACTTCTGGATCCTCCTCGTCGTCCGCAAACCGGCATCGTTGATGAATGTGTTTCGGTCCTGTAAGTCAGTCCCCCCCCCCCC
Part 3 CCCCCCCCCCCCCCCCCTGACTGAAGACCTAGGAGGAGCAGCAGCAGGCGTTTGGCCGTAGCAACTACTTACGACAAAAGCCAGGACATTCAGTCAG
                            BamHI                                                  AvaII 51 52 53 54 55 56 57 58 59 60 61 62 63 64 65 66 67 68 69 70
          SerCysAspLeuArgArgLeuGluMetTyrCysAlaProLeuLysProAlaLysSerAlaTer
       TGACTGACTTGGTCCTGTGACCTTCGCCGTCTGGAAATGTACTGCCTCCGCTGAAACCGGCTAAGTCTGCATAGTCGACTCAAGTCAGTCCCCCCCCCCCC
Part 4 CCCCCCCCCCCCCACTGACTGAACCAGGACACTGGAAGCGGCAGACCTTTGGCCGATTCAGACGCGACTTTGGCCGAGGCGACTTTGGCCGATTCAGACGTATCAGCTGAGTTCAGTCAG
                             AvaII                                                    SalI
```

```
met lys ala ile phe val leu lys gly ser leu asp arg asp leu asp ser arg ile glu
ATG AAA GCA ATT TTC GTA CTG AAA GGT TCA CTG GAC AGA GAT CTC GAC AGC CGT ATT GAA leu glu met arg thr asp his lys glu leu ser glu his leu met leu val asp leu ala
CTG GAA ATG CGT ACC GAT CAT AAA GAG CTG TCT GAA CAT CTG ATG CTG GTT GAT CTC GCC arg asn asp leu ala arg ile cys thr pro gly ser arg tyr val ala asp leu thr lys
CGT AAT GAT CTG GCA CGC ATT TGC ACC CCC GGC AGC CGC TAC GTC GCC GAT CTC ACC AAA val asp arg tyr ser tyr val met his leu val ser arg val val gly glu leu arg his
GTT GAC CGT TAT TCC TAT GTG ATG CAC CTC GTC TCT CGC GTA GTC GGC GAA CTG CGT CAC asp leu asp ala leu his ala tyr arg ala cys met asn met gly thr leu ser gly ala
GAT CTT GAC GCC CTG CAC GCT TAT CGC GCC TGT ATG AAT ATG GGG ACG TTA AGC GGT GCG pro lys val arg ala met gln leu ile ala glu ala glu gly arg arg arg gly ser tyr
CCG AAA GTA CGC GCT ATG CAG TTA ATT GCC GAG GCG GAA GGT CGT CGC CGC GGC AGC TAC gly gly ala val gly tyr phe thr ala his gly asp leu asp thr cys ile val ile arg
GGC GGC GCG GTA GGT TAT TTC ACC GCG CAT GGC GAT CTC GAC ACC TGC ATT GTG ATC CGC ser ala leu val glu asn gly ile ala thr val gln ala gly ala gly val val leu asp
TCG GCG CTG GTG GAA AAC GGT ATC GCC ACC GTG CAA GCG GGT GCT GGT GTA GTC CTT GAT ser val pro gln ser glu ala asp glu thr arg asn lys ala arg ala val leu arg ala
TCT GTT CCG CAG TCG GAA GCC GAC GAA ACC CGT AAC AAA GCC CGC GCT GTA CTG CGC GCT ile ala thr ala his his ala gln glu phe |pro ala gly pro| glu thr leu cys gly ala
ATT GCC ACC GCG CAT CAT GCA CAG GAA TTC |CCT GCC GGT CCG| GAA ACT CTG TGC GGC GCT glu leu val asp ala leu gln phe val cys gly asp arg gly phe tyr phe asn lys pro
GAG CTG GTT GAC GCT CTG CAG TTC GTA TGT GGT GAT CGA GGC TTC TAC TTC AAC AAA CCG thr gly tyr gly ser ser ser arg arg ala pro gln thr gly ile val asp glu cys cys
ACT GGG TAC GGA TCC TCC TCT CGT CGT GCT CCG CAA ACC GGC ATC GTT GAT GAA TGC TGT phe arg ser cys asp leu arg arg leu glu met tyr cys ala pro leu lys pro ala lys
TTT CGG TCC TGT GAC CTT CGC CGT CTG GAA ATG TAC TGC GCT CCG CTG AAA CCG GCT AAG ser ala AM
TCT GCA TAG TCGACGTACATGAA
```

Translated Mol. Weight = 28671.51

Underscored – Mature Human IGF-1

Boxed – Collagenase Recognition Site sLE-IGF-1 Fusion Protein

Fig. 8.

```
            1                                          10
            met lys ala ile phe val leu lys gly ser leu asp arg asp pro glu phe
            ATG AAA GCA ATT TTC GTA CTG AAA GGT TCA CTG GAC AGA GAT CCA GAA TTC
            20                                         30
┌─────────────────┐
│pro ala gly pro  │glu thr leu cys gly ala glu leu val asp ala leu gln phe val cys
│CCT GCC GGT CCG  │GAA ACT CTG TGC GGC GCT GAG CTG GTT GAC GCT CTG CAG TTC GTA TGT
└─────────────────┘
            40                                         50
gly asp arg gly phe tyr phe asn lys pro thr gly tyr gly ser ser ser arg arg ala
GGT GAT CGA GGC TTC TAC TTC AAC AAA CCG ACT GGG TAC GGA TCC TCC TCT CGT CGT GCT
            60                                         70
pro gln thr gly ile val asp glu cys cys phe arg ser cys asp leu arg arg leu glu
CCG CAA ACC GGC ATC GTT GAT GAA TGC TGT TTT CGG TCC TGT GAC CTT CGC CGT CTG GAA
            80                                89
met tyr cys ala pro leu lys pro ala lys ser ala AM
ATG TAC TGC GCT CCG CTG AAA CCG GCT AAG TCT GCA TAG
```

Underscored – Mature Human IGF-1

Boxed – Collagenase Recognition Site

Yeast prepro α factor – IGF-1

Fig. 10.

```
met arg phe pro ser ile phe ser ala val leu phe ala ala ser ser ala leu ala ala
ATG AGA TTT CCT TCA ATT TTT AGT GCA GTT TTA TTC GCA GCA TCC TCC GCA TTA GCT GCT pro val asn thr thr thr glu asp glu thr ala gln ile pro ala glu ala val ile gly
CCA GTC AAC ACT ACA ACA GAA GAT GAA ACG GCA CAA ATT CCG GCT GAA GCT GTC ATC GGT tyr ser asp leu glu gly asp phe asp val ala val leu pro phe ser asn ser thr asn
TAC TCA GAT TTA GAA GGG GAT TTC GAT GTT GCT GTT TTG CCA TTT TCC AAC AGC ACA AAT asn gly leu leu phe ile asn thr thr ile ala ser ile ala ala lys glu glu gly val
AAC GGG TTA TTG TTT ATA AAT ACT ACT ATT GCC AGC ATT GCT GCT AAA GAA GAA GGG GTA ser leu asp lys arg glu ala glu ala leu glu phe  pro ala gly pro  glu thr leu cys
TCT TTG GAT AAA AGA GAG GCT GAA GCT CTA GAA TTC CCT GCC GGT CCG  GAA ACT CTG TGC gly ala glu leu val asp ala leu glu phe val cys gly asp arg gly phe tyr phe asn
GGT GCT GAA CTG GTT GAC GCT CTG GAG TTC GTA TGT GGT GAC CGT GGC TTT TAC TTC AAC lys pro thr gly tyr gly ser ser ser arg arg ala pro gln thr gly ile val asp glu
AAA CCG ACT GGT TAC GGA TCC TCC TCT CGT CGC GCT CCG CAA ACT GGC ATC GTT GAT GAA cys cys phe arg ser cys asp leu arg arg leu glu met tyr cys ala pro leu lys pro
TGC TGT TTT CGT TCT TGT GAC CTG CGC CGT CTG GAA ATG TAC TGC GCT CCG CTG AAA CCG ala lys ser ala Term
GCT AAG TCT GCA TAG
```

Underscored – Mature Human IGF-1

Boxed – Collagenase Recognition Site

Fig.12.

Yeast Invertase Signal - IGF-1 Protein

```
                1                                                          10
                met leu leu gln ala phe leu phe leu ala gly phe ala ala lys ile
                ATG CTT TTG CAA GCT TTC CTT TTC TTG GCT GGT TTT GCA GCC AAA ATA 20                                                        30
ser ala gly pro glu thr leu cys gly ala glu leu val asp ala leu gln phe val cys
TCT GCA GGT CCG GAA ACT CTG TGC GGC GCT GAG CTG GTT GAC GCT CTG CAG TTC GTA TGT 40                                                        50
gly asp arg gly phe tyr phe asn lys pro thr gly tyr gly ser ser ser arg arg ala
GGT GAT CGA GGT TTC TAC TTC AAC AAA CCG ACT GGG TAC GGA TCC TCC TCT CGT CGT GCT 60                                                        70
pro gln thr gly ile val asp glu cys cys phe arg ser cys asp leu arg arg leu glu
CCG CAA ACC GGC ATC GTT GAT GAA TGC TGT TTT CGG TCC TGT GAC CTT CGC CGT CTG GAA 80                                            89
met tyr cys ala pro leu lys pro ala lys ser ala AM
ATG TAC TGC GCT CCG CTG AAA CCG GCT AAG TCT GCA TAG
```

Underscored - Mature Human IGF-1

HUMAN EGF

```
ecoRI                                           rsaI
GAATTCATGA ACTCTGACTC TGAATGTCCA TTATCGCATG ATGGGT
CTTAAGTACT TGAGACTGAG ACTTACAGGT AATAGCGTAC TACCCA rsaI              hinfI     hinfI              xbaI
  ACTG TTTGCACGAC GG        AGTCTGTA TGTATATTGA AGCT
  TGAC AAACGTGCTG CCTCA       GACAT ACATATAACT TCGAGATC sau3AI
xbaI                                                    bglII
  CTAGAC AAGTACGCTT GTAACTGTGT TGTTGGTTAC ATCGGTGAAA GATGTCAATA CAGA
      TG TTCATGCGAA CATTGACACA ACAACCAATG TAGCCACTTT CTACAGTTAT GTCTCTAG sau3AI
bglII                                      claI     hindIII
  GATCTA AAGTGGTGGG AATTGAGATA GATTGAATTG AATTGAAATC GATTAAAGCT T
      AT TTCACCACCC TTAACTCTAT CTAACTTAAC TTAACTTTAG CTAATTTCGA A
```

Yeast prepro α factor - EGF

```
met arg phe pro ser ile phe ser ala val leu phe ala ala ser ser ala leu ala ala
ATG AGA TTT CCT TCA ATT TTT AGT GCA GTT TTA TTC GCA GCA TCC TCC GCA TTA GCT GCT pro val asn thr thr glu asp glu thr ala gln ile pro ala glu ala val ile gly
CCA GTC AAC ACT ACA GAA GAT GAA ACG GCA CAA ATT CCG GCT GAA GCT GTC ATC GGT tyr ser asp leu glu gly asp phe asp val ala val leu pro phe ser asn ser thr asn
TAC TCA GAT TTA GAA GGG GAT TTC GAT GTT GCT GTT TTG CCA TTT TCC AAC AGC ACA AAT asn gly leu phe ile asn thr thr ile ala ser ile ala ala lys glu glu gly val
AAC GGG TTA TTG TTT ATA AAT ACT ACT ATT GCC AGC ATT GCT GCT AAA GAA GAA GGG GTA ser leu asp lys arg asn ser asp ser glu cys pro leu ser his asp gly tyr cys leu
TCT TTG GAT AAA AGA AAC TCT GAC TCT GAA TGT CCA TTA TCG CAT GAT GGG TAC TGT TTG his asp gly val cys met tyr ile glu ala leu asp lys tyr ala cys asn cys val val
CAC GAC GGA GTC TGT ATG TAT ATT GAA GCT CTA GAC AAG TAC GCT TGT AAC TGT GTT GTT gly tyr ile gly glu arg cys gln tyr arg asp leu lys trp trp glu leu arg AM
GGT TAC ATC GGT GAA AGA TGT CAA TAC AGA GAT CTA AAG TGG TGG GAA TTG AGA TAG
```

Fig. 17.

Yeast Preinvertase - EGF

```
            -19
            met leu leu gln ala phe leu phe leu ala gly phe ala ala lys ile
GAATTCATG   ATG TTG TTG CAA GCT TTC TTG TTC TTG GCT GGT TTC GCT GCT AAG ATC
             1                                10
ser ala asn ser asp ser glu cys pro leu ser his asp gly tyr cys leu his asp gly
TCT GCT AAC TCT GAC TCT GAA TGT CCA TTA TCG CAT GAT GGG TAC TGT CTG CAC GAC GGA
            20                                30
val cys met tyr ile glu ala leu asp lys tyr ala cys asn cys val val gly tyr ile
GTC TGT ATG TAC ATT GAA GCT CTA GAC AAG TAC GCT TGT AAC TGT GTT GTT GGT TAC ATC
            40                                50             53
gly glu arg cys gln tyr arg asp leu lys trp glu leu arg AM
GGT GAA AGA TGT CAA TAC AGA GAT CTA AAG TGG GAA TTG AGA TAG ATTGAATTGAATTGA

AATCGATTAAAGCTT
```

Fig. 18.

Human IGF-II coding sequence

```
                      1
                      met ala tyr arg pro ser glu thr leu cys gly gly glu leu val asp thr
TCTAGAATT             ATG GCT TAT CGA CCA TCT GAA ACC TTG TGT GGT GGT GAG CTG GTG GAC ACC
        20                                          30
leu gln phe val cys gly asp arg gly phe tyr phe ser arg pro ala ser arg val ser
CTC CAG TTC GTC TGT GGG GAC CGC GGT TTC TAC TTC TCT AGG CCC GCA AGC CGT GTG AGC
        40                                          50
arg arg ser arg gly ile val glu glu cys cys phe arg ser cys asp leu ala leu leu
CGT CGC AGT CGT GGC ATC GTT GAG GAG TGC TGT TTC CGC AGC TGT GAC CTG GCC CTA TTG
        60                                          68
glu thr tyr cys ala thr pro ala lys ser glu AM
GAA ACC TAC TGT GCT ACC CCA GCT AAG TCT GAA TAG GATCC
```

| Carboxy terminus of α-factor: | Gly | -- | Gln | -- | Pro | -- | Met | -- | Tyr COOH |
|---|---|---|---|---|---|---|---|---|---|
| Possible codons and their usage | GGU (90) GGC (3) GGA (0) GGG (0) | | CAA (20) CAG (0) | | CCA (32) CCU (3) CCC (1) CCG (0) | | AUG (20) | | UAC (33) UAU (0) |

Consensus oligonucleotides:  5'-GG$^T_C$CAACC$^A_T$ATGTAC

Synthesized oligonucleotide pools complementary to above:
I.  5'-GTACATTGGTTG$^A_G$CC
II. 5'-GTACATAGGTTG$^A_G$CC

Fig.19.

```
CGACAGTAAATTTTGCCGAATTTAATAGCTTCTACTGAAAAACAGTGGACCATGTGAAAAGATGCATCTCATTATCAA
         -280                    -260                    -240                    -220
ACACATAATATTCAAGTGAGCCTTACTTCAATTGTATTGAAGTGCAAGAAAACCAAAAAGCAACAACAGGTTTTGGATA
         -200                    -180                    -160                    -140
AGTACATATATAAGAGGGCCCTTTTGTTCCCATCAAAAATGTTACTGTCTTACGATTCATTTACGATTCAAGAATAGTT
         -120                    -100                    -80                     -60
CAAACAAGAAGATTACAAACTATCAATTTCATACACAATATAAACGATTAAAAGA ATG AGA TTT CCT TCA ATT
         -40                     -20                              Met Arg Phe Pro Ser Ile
                                                                   1

Phe Thr Ala Val Leu Phe Ala Ala Ser Ser Ala Leu Ala Ala Pro Val Ala Ala Asn Thr Thr Thr
TTT ACT GCA GTT TTA TTC GCA GCA TCC TCC GCA TTA GCT GCT CCA GTC AAC ACT ACA ACA
         20                      40                      60

Glu Asp Glu Thr Ala Ala Gln Ile Pro Ala Glu Ala Val Ile Gly Tyr Leu Asp Leu Glu Gly
GAA GAT GAA ACG GCA CAA ATT CCG GCT GAA GCT GTC ATC GGT TAC TTA GAT TTA GAA GGG
         80                      100                     120

Asp Phe Asp Val Ala Val Leu Pro Phe Ser Asn Ser Thr Asn Asn Gly Leu Leu Phe Ile
GAT TTC GAT GTT GCT GTT TTG CCA TTT TCC AAC AGC ACA AAT AAC GGG TTA TTG TTT ATA
         140                     160                     180

Asn Thr Thr Ile Ala Ser Ile Ala Ala Lys Glu Gly Val Ser Leu Asp Lys Arg Glu
AAT ACT ACT ATT GCC AGC ATT GCT GCT AAA GAA GAA GGG GTA TCT TTG GAT AAA AGA GAG
         200                     220                     240
```

Fig. 21A.

```
Ala Glu Ala Trp His Trp Leu Gln Leu Lys Pro Gly Gln Pro Met Tyr Lys Arg Glu Ala
GCT GAA GCT TGG CAT TGG CTT CAA CTA AAA CCT GGC CAA CCA ATG TAC AAG AGA GAA GCC
        260                 280          100        300              *
Glu Ala Glu Ala Trp His Trp Leu Gln Leu Lys Pro Gly Gln Pro Met Tyr Lys Arg Glu
GAA GCT GAA GCT TGG CAT TGG CTG CAA CTA AAG CCT GGC CAA CCA ATG TAC AAA AGA GAA
        320                 340         120 *  *   *          *   *       *
Ala Asp Ala Glu Ala Trp His Trp Leu Gln Leu Lys Pro Gly Gln Pro Met Tyr Lys Arg
GCC GAC GCT GAA GCT TGG CAT TGG CTG CAA CTA AAG CCT GGC CAA CCA ATG TAC AAA AGA
        380                 400   *  *  140*  *   *          *    *        *
Glu Ala Asp Ala Glu Ala Trp His Trp Leu Gln Leu Lys Pro Gly Gln Pro Met Tyr End
GAA GCC GAC GCT GAA GCT TGG CAT TGG TTG CAG TTA AAA CCC GGC CAA CCA ATG TAC TAA
        440                 460          *  *   *    *160     *  *  *   *  *
GCCCGACTGATAACAACAGTGTAGATGTAACAAAGTCGACTTTGTTCCCACTGTACTTTTAGCTCGTACAAAATACAAT
        500                 520                 540                 560
ATACTTTTCATTTCTCCGTAAACAACATGTTTTCCCATGTAATATCCTTTTCTATTTTCGTTCCGTTACCAACTTTAC
        580                 600                 620                 640
ACATACTTTATATAGCTATTCACTTCTATACACTAAAAAAACTAAGACAATTTAATTTTGCTGCCTGCCATATTTCAAT
        660                 680                 700                 720
TTGTTATAAATTCCTATAATTTATCCTATTAGTAGCTAAAAAAAGATGAATGTGAATCGAATCCTAAGAGAATTC
        740                 760                 780                 800
```

*Fig.21B.*

```
TTCTTCATTGGTACATCAATGCCAGCAACGATGTGCGCATCTGGGCGACGCCTGTAGTGATTGTTTTCAAGGTATCGAG
       -300              -280              -260              -240

CCAAACTATTCATCGTTACTGTTTCAAATATTCAGTTGTTTCAGTACAGAGTCGCCGTGGACCTAGTGAAACTTGGTGT
       -220              -200              -180              -160

CTTTACAGCGCAGAGACGAGGGCTTATATGTATAAAAGCTGTCCTTGATTCTGGTGTAGTTTGAGGTGTCCTTCCTATA
       -140              -120              -100               -80

TCTGTTTTTATATTCTATATAATGGATAATTACTACCATCACCTGCATCAAATTCCAGTAAATTCACATATTGGAGAAA
       -60               -40               -20
```

```
  1                                      10                                      20
Met  Lys  Phe  Ile  Ser  Thr  Phe  Leu  Thr  Phe  Ile  Leu  Ala  Ala  Val  Ser  Val  Thr  Ala  Ser
ATG  AAA  TTC  ATT  TCT  ACC  TTT  CTC  ACT  TTT  ATT  TTA  GCG  GCC  GTT  TCT  GTC  ACT  GCT  AGT
  1                    20                                      40                                      60

30                                      40
Ser  Asp  Glu  Asp  Ile  Ala  Gln  Val  Pro  Ala  Glu  Ala  Ile  Ile  Gly  Tyr  Leu  Asp  Phe  Gly
TCC  GAT  GAA  GAT  ATC  GCT  CAG  GTG  CCA  GCC  GAG  GCC  ATT  ATT  GGA  TAC  TTG  GAT  TTC  GGA
                       80                                      100                                     120

50                                      60
Gly  Asp  His  Asp  Ile  Ala  Phe  Leu  Pro  Phe  Ser  Asn  Ala  Thr  Ala  Ser  Gly  Leu  Leu  Phe
GGT  GAT  CAT  GAC  ATA  GCT  TTT  TTA  CCA  TTC  AGT  AAC  GCT  ACC  GCC  AGT  GGG  CTA  TTG  TTT
                       140                                     160                                     180

70                                      80
Ile  Asn  Thr  Thr  Ile  Ala  Glu  Ala  Ala  Glu  Lys  Glu  Gln  Asn  Thr  Thr  Leu  Ala  Lys  Arg
ATC  AAC  ACC  ACT  ATT  GCT  GAG  GCG  GCT  GAA  AAA  GAG  CAA  AAC  ACC  ACT  TTG  GCG  AAA  AGA
                       200                                     220                                     240

90                                      100
Glu  Ala  Val  Ala  Asp  Ala │Trp  His  Trp  Leu  Asn  Leu  Arg  Pro  Gly  Gln  Pro  Met  Tyr│Lys
GAG  GCT  GTT  GCC  GAC  GCT │TGG  CAC  TGG  TTA  AAT  TTG  AGA  CCA  GGC  CAA  CCA  ATG  TAC│AAG
                              *         * *
                       260                                     280                                     300

110                                     120
Arg  Glu  Ala  Asn  Ala  Asp  Ala │Trp  His  Trp  Leu  Gln  Leu  Lys  Pro  Gly  Gln  Pro  Met  Tyr│
AGA  GAG  GCC  AAC  GCT  GAT  GCT │TGG  CAC  TGG  TTG  CAA  CTC  AAG  CCA  GGC  CAA  CCA  ATG  TAC│
                                    *         * *
                       320                                     340                                     360
```

```
End
TGA  AAAATGACCCTAAACTACTTCTAAACCCTCTCGATTTCTTTCACGTTCATACAACACCTAGTTTTATTTATTTTC
            380               400               420

TTTTCAATCTGAGTAGTTGAGTTTTCGATCACTCACATAGAACTATTTTTTGCCATTTAAATAAAGTATTCTCTCAAAT
    440               460               480               500

GATGCGATACTATAATACTCTTTGCCATATATTACATTCATTCATAAATAGGCTATGTTTCTATATCCGTTTCCGATTC
    520               540               560               580

TGTCTGCAAGCAAGGTTCCCTATCATTACCGGATTGTTCACTATGGTTGGAGCTC
    600               620               640
```

Fig.22.

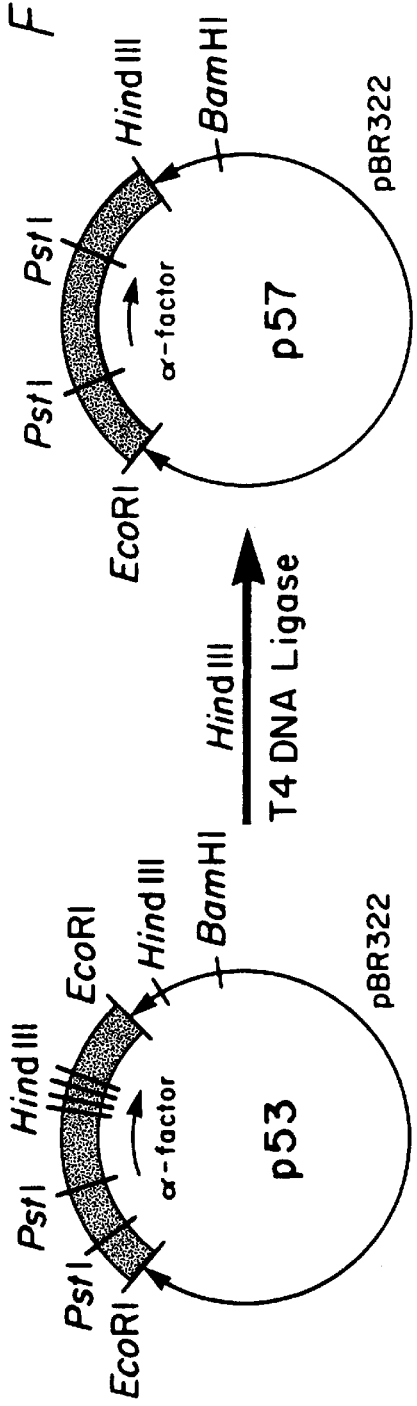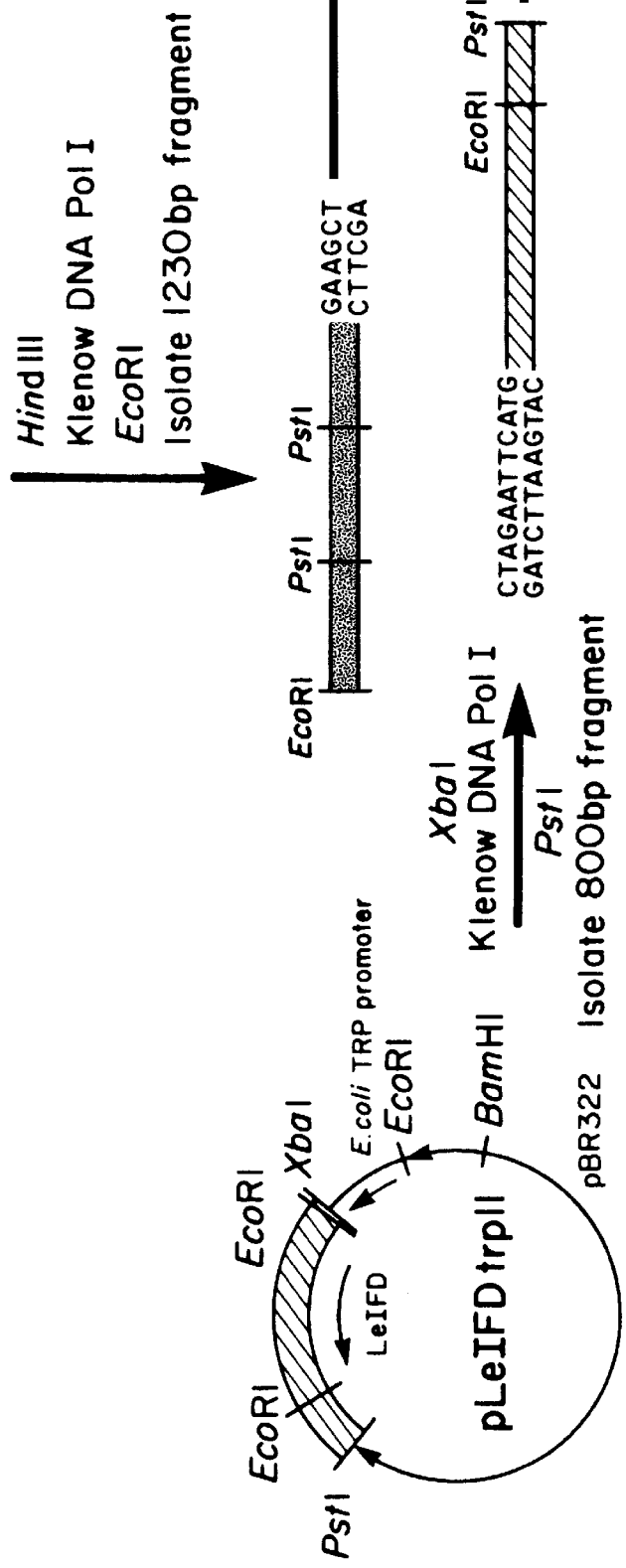
Fig. 23A.

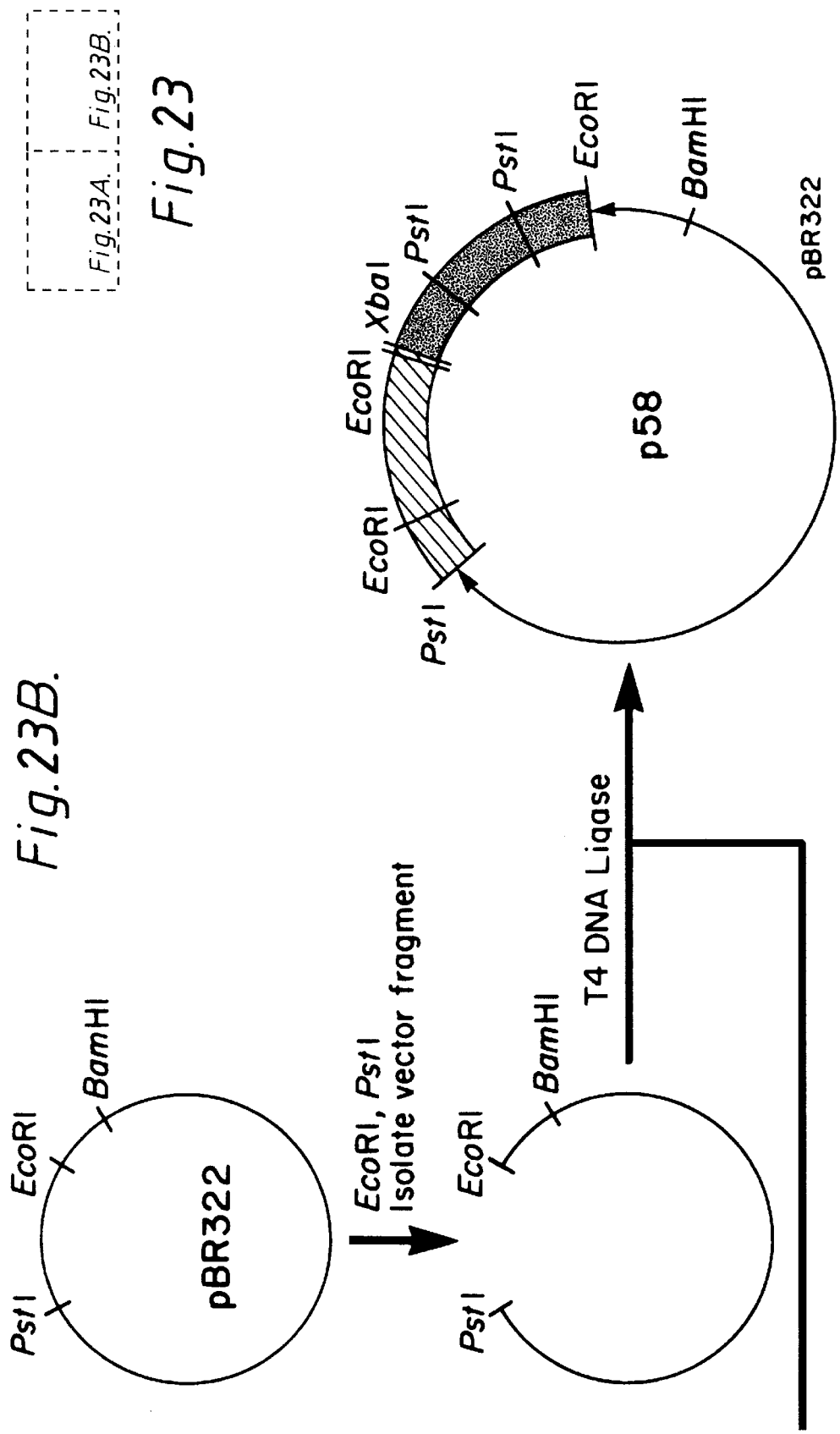

PREPARATION OF HUMAN IGF VIA RECOMBINANT DNA TECHNOLOGY

CROSS REFERENCE TO RELATED APPLICATIONS

This application is related to commonly assigned applications filed concurrently herewith under U.S. Ser. Nos. 506,077 abandoned and 506,098 abandoned, and their parents U.S. Ser. Nos. 501,351 abandoned and 501,362 abandoned.

This is a continuation of application Ser. No. 06/506,078 filed on Jun. 20, 1983, abandoned, which is a continuation-in-part of Ser. No. 06/501,353 filed Jun. 6, 1983, now abandoned, which applications are incorporated herein by reference and to which applications priority is claimed under 35 USC §120.

FIELD OF THE INVENTION

This invention relates to the preparation of human IGF (insulin-like growth factor), in various forms, via recombinant DNA technology. Notably, the present invention provides for the preparation of human IGF as a mature protein product of expression, processing, and secretion in a recombinant DNA modified host organism. This invention thus provides for the production, isolation, and use of human IGF, in its various forms, as well as to the associated recombinant DNA technology by which it is prepared. In addition, the present invention relates to the similar preparation of a related protein, human EGF (Epidermal Growth Factor).

The present invention arises in part from the discovery of a novel system by which human IGF can be prepared by a recombinant host organism in the form of a discrete, mature protein. This is accomplished according to one aspect of the present invention by an expression system which permits the expression of the amino acid sequence of human IGF fused with at least a portion of the yeast alpha factor signal sequence, followed by processing of said signal sequence, and secretion of mature human IGF protein into the medium supporting the host organism. Thus, this novel aspect of the present invention, it is believed for the first time, permits the preparation, isolation, and utilization of human IGF as a discrete, mature protein. The present invention, in its broad compass, however, covers the preparation of the amino acid sequence of human IGF in other recombinant systems including bacteria and cell culture and includes, therefore, the expression of human IGF DNA sequences providing not only mature human IGF but also fusion product derivatives containing the amino acid sequence of IGF as the essential component. All such products have been found to be biologically active, hence useful as intended.

The publications and other materials hereof used to illuminate the background of the invention, and in particular cases, to provide additional details concerning its practice are incorporated herein by this reference and for convenience, are alphabetically and numerically referenced in the following text and respectively grouped in the appended bibliography.

BACKGROUND OF THE INVENTION

A. Human IGF (Insulin-like Growth Factor)

Human IGF has been the subject of a fair amount of intensive study by past workers. A body of literature has been developed related to various aspects of this protein or series of proteins (see references A through L).

Insulin-like growth factors I and II have been isolated from human serum (A). The designation "insulin-like growth factor" or IGF was chosen to express the insulin-like effects and the insulin-like structure of these polypeptides which act as mitogens on a number of cells. The complete amino acid sequences of IGF-I and IGF-II have been determined (D,E). They are both single-chain polypeptides with three disulphide bridges and a sequence identity of 49 and 47 percent respectively, to human insulin A and B chains. The connecting peptide or C region is considerably shorter than the one of proinsulin and does not show any significant homology to it. (For a summary of earlier studies on the biological efforts of IGF, see Reference F).

IGF-I and IGF-II are growth promoting polypeptides occurring in human serum and human cerebral spinal fluid. Their structure is homologous to proinsulin. IGF-I seems to be produced by the liver along with a specific IGF-binding protein both of which are under control of growth hormone. Thus, human IGF is considered to be an active growth promoting molecule that mediates the effect of human growth hormone.

It was perceived that the application of recombinant DNA and associated technologies would be a most effective way of providing the requisite large quantities of high quality human IGF for applied use to human beings as a growth factor. The goal was to produce human IGF either as biologically active fusion protein, or more importantly, as a mature protein, as products of recombinant DNA technology from a host organism. Such materials would exhibit bioactivity admitting of their use clinically in the treatment of various growth affected conditions.

B. Recombinant DNA Technology

Recombinant DNA technology has reached the age of some sophistication. Molecular biologists are able to recombine various DNA sequences with some facility, creating new DNA entities capable of producing copious amounts of exogenous protein product in transformed microbes and cell cultures. The general means and methods are in hand for the in vitro ligation of various blunt ended or "sticky" ended fragments of DNA, producing potent expression vehicles useful in transforming particular organisms, thus directing their efficient synthesis of desired exogenous product. However, on an individual product basis, the pathway remains somewhat tortuous and the science has not advanced to a stage where regular predictions of success can be made. Indeed, those who portend successful results without the underlying experimental basis, do so with considerable risk of inoperability.

DNA recombination of the essential elements, i.e., an origin of replication, one or more phenotypic selection characteristics, an expression promoter, heterologous gene insert and remainder vector, generally is performed outside the host cell. The resulting recombinant replicable expression vehicle, or plasmid, is introduced into cells by transformation and large quantities of the recombinant vehicle are obtained by growing the transformant. Where the gene is properly inserted with reference to portions which govern the transcription and translation of the encoded DNA message, the resulting expression vehicle is useful to actually produce the polypeptide sequence for which the inserted gene codes, a process referred to as expression. The resulting product may be obtained by lysing, if necessary, the host cell, in microbial systems, and recovering the product by appropriate purification from other proteins.

In practice, the use of recombinant DNA technology can express entirely heterologous polypeptides-so-called direct expression-or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment. See references (M) and (N).

Similarly, the art of cell or tissue cultures for studying genetics and cell physiology is well established. Means and methods are in hand for maintaining permanent cell lines, prepared by successive serial transfers from isolated normal cells. For use in research, such cell lines are maintained on a solid support in liquid medium, or by growth in suspension containing support nutriments. Scale-up for large preparations seems to pose only mechanical problems. For further background, attention is directed to references (O) and (P).

Likewise, protein biochemistry is a useful, indeed necessary, adjunct in biotechnology. Cells producing the desired protein also produce hundreds of other proteins, endogenous products of the cell's metabolism. These contaminating proteins, as well as other compounds, if not removed from the desired protein, could prove toxic if administered to an animal or human in the course of therapeutic treatment with desired protein. Hence, the techniques of protein biochemistry come to bear, allowing the design of separation procedures suitable for the particular system under consideration and providing a homogeneous product safe for intended use. Protein biochemistry also proves the identity of the desired product, characterizing it and ensuring that the cells have produced it faithfully with no alterations or mutations. This branch of science is also involved in the design of bioassays, stability studies and other procedures necessary to apply before successful clinical studies and marketing can take place.

SUMMARY OF THE INVENTION

The present invention is based upon the discovery that recombinant DNA technology can be used successfully to produce human IGF and related protein, human EGF, preferably in direct form and in amounts sufficient to initiate and conduct animal and clinical testing as prerequisites to market approval. The products human IGF and EGF are suitable for use in all of their forms as produced according to the present invention, viz. in tie prophylactic or therapeutic treatment of human beings for various growth associated conditions or diseases. Accordingly, the present invention, in one important aspect, is directed to methods of treating growth conditions in human subjects using human IGF or human EGF, and suitable pharmaceutical compositions thereof, prepared in accordance with the methods and means of the present invention.

The present invention further comprises essentially pure, mature human IGF, as a product of expression, processing, and secretion in a recombinant host organism. Such human IGF is free from association with N-terminus amino acid sequence derivable from the expression systems that can be employed to prepare the material. Thus, while the present invention is directed to the preparation of polypeptides comprising the amino acid sequence of IGF, a notable aspect of the present invention involves the production of the mature human IGF directly into the medium of the recombinant host organism employed. The present invention is also directed to replicable DNA expression vehicles harboring gene sequences encoding human IGF and human EGF in expressible form, to microorganism strains or cell cultures transformed with such vehicles and to microbial or cell cultures of such transformants capable of producing amino acid sequences of human IGF and human EGF. In still further aspects, the present invention is directed to various processes useful for preparing said gene sequences, DNA expression vehicles, microorganisms and cell cultures and specific embodiments thereof. Still further, this invention is directed to the preparation of fermentation cultures of said microorganisms and cell cultures.

BRIEF DESCRIPTION OF THE DRAWINGS

FIG. 1 represents the chemically synthesized DNA strands used in the construction of expression vectors for human IGF.

FIG. 2 shows the completed double stranded DNA of FIG. 1.

FIG. 3 show the fragments of DNA of FIG. 2 after restriction by EcoRI and PstI and Bam HI.

FIG. 5 show parts 3 and 4 of IGF-I right half.

FIG. 7 shows a sequence of DNA and deduced fusion protein containing IGF-I.

FIG. 8 shows a sequence of DNA and deduced short fusion protein containing IGF-I.

FIG. 10 shows the DNA and protein sequence of IGF-I fused with alpha factor pre-pro sequence.

FIG. 12 shows the yeast invertase signal fused to IGF-I.

FIG. 15 is the synthetic DNA used to construct the coding sequence of mature human EGF.

FIG. 16 depicts the yeast alpha factor "pre-pro" sequence fused to the human EGF coding sequence.

FIG. 17 depicts the yeast invertase signal sequence fused to the human EGF coding sequence.

FIG. 18 shows the coding sequence for human IGF-II.

FIG. 19 illustrates the structure of pools of synthetic oligonucleotides used as hybridization probes to isolate the gene for α-factor.

FIGS. 21A and 21B and 22 are the nucleotide sequences of α-factor genes.

FIGS. 23A and 23B illustrates the scheme for joining the gene for human interferon D with the gene for the α-factor promoter and signal sequence.

DETAILED DESCRIPTION

A. Definitions

Figure 4:
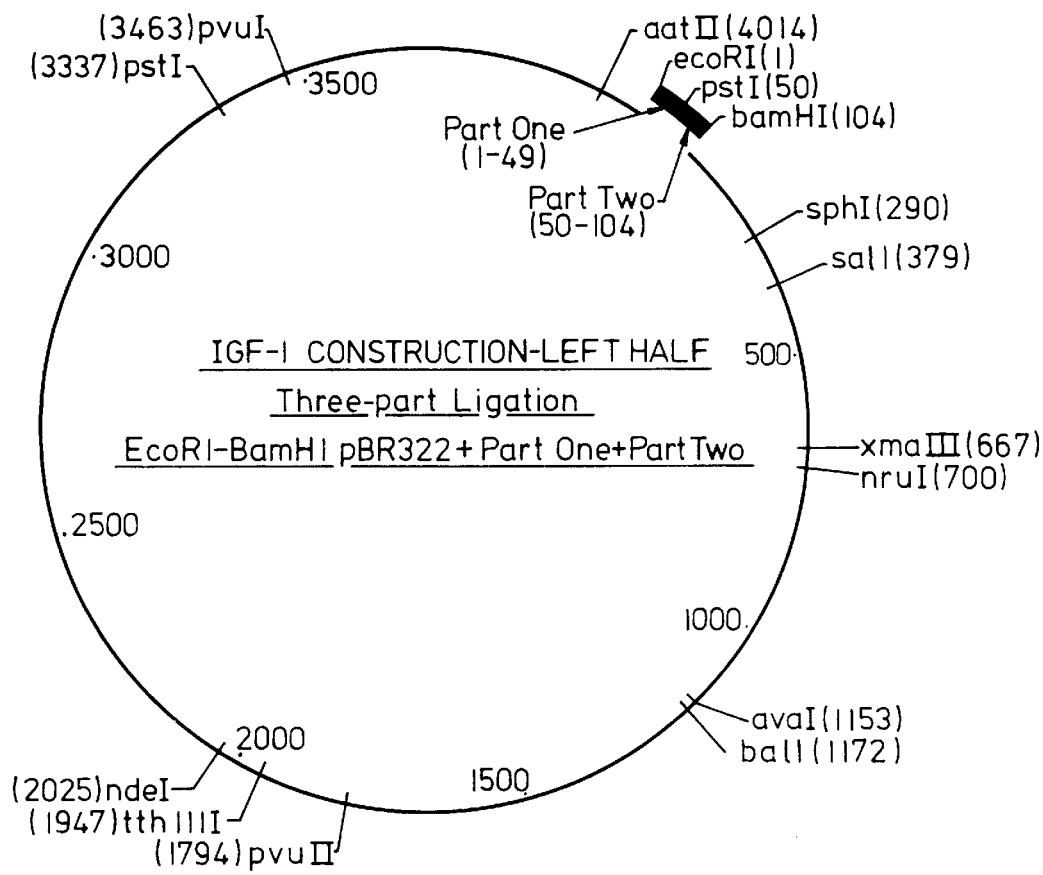
FIG. 4 depicts the ligation of parts 1 and 2 of FIG. 3 into PBR322.

As used herein, "human IGF" and "human EGF" denotes human insulin-like growth factor and human epidermal growth factor, produced by microbial or cell culture systems and bioactive forms comprising the amino acid sequence corresponding to human IGF and human EGF otherwise native to human tissue. The human IGF and EGF proteins produced herein have been defined by means of DNA, gene, and deductive amino acid sequencing. It will be understood that inasmuch as natural allelic variations exist and occur from individual to individual, as demonstrated by (an) amino acid difference(s) in the overall sequence or by deletions, substitutions, insertions, inversions, or additions of one or more amino acids of said sequences, the present invention is intended to embrace all of such allelic variations of the two molecules involved. In addition, the location of and the degree of glycosylation depend upon the nature of the recombinant host organism employed and such variations as may occur are included within the ambit of this invention. Finally, the potential exists in the use of DNA technology for the preparation of various derivatives of human IGF and human EGF by simple modification of the underlying gene sequence for such molecules. Such modifications could be accomplished by means of site directed mutagenesis of the underlying DNA, as an example. All such modifications resulting in derivatives of human IGF and human EGF are included within the scope of the present invention so long as the essential characteristic human IGF and human EGF activities remain unaffected in kind.

"Essentially pure form" when used to describe the state of human IGF or human EGF produced by this invention means that the proteins are free of proteins or other materials normally associated with human IGF or human EGF when produced by non-recombinant cells, i.e. in their "native" environments.

"Expression vector" includes vectors which are capable of expressing DNA sequences contained therein, where such sequences are operably linked to other sequences capable of effecting their expression, i.e., promotor/operator sequences. In sum, "expression vector" is given a functional definition: any DNA sequence which is capable of effecting expression of a specified DNA code disposed therein. In general, expression vectors of utility in recombinant DNA techniques are often in the form of "plasmids" which refer to circular double stranded DNA loops which in their vector form are not bound to the chromosone. In the present specification, "plasmid" and "vector" are used interchangably as the plasmid is the most commonly used form of vector. However, the invention is intended to include such other forms of expression vectors which function equivalently and which become known in the art subsequently.

"Recombinant host cells" refers to cells which have been transformed with such vectors. Thus, the human IGF and human EGF molecules produced by such cells can be referred to as "recombinant human IGF" and "recombinant human EGF".

B. Host Cell Cultures and Vectors

The vectors and methods disclosed herein are suitable for use in host cells over a wide range of prokaryotic and eukaryotic organisms.

In general, of course, prokaryotes are preferred for cloning of DNA sequences in constructing the vectors useful in the invention. For example, $E. coli$ K12 strain 294 (ATCC No. 31446) is particularly useful. Other microbial strains which may be used include $E. coli$ strains such as $E. coli$ B, and $E. coli$ X1776 (ATTC No. 31537). The aforementioned strains, as well as $E. coli$ W3110 (F$^-$, $\lambda^-$, prototrophic, ATTC No. 27325), bacilli such as $Bacillus\ subtilus$, and other enterobacteriaceae such as $Salmonella\ typhimurium$ or $Serratia\ marcesans$, and various pseudomonas species may be used. These examples are, of course, intended to be illustrative rather than limiting.

In general, plasmid vectors containing replicon and control sequences which are derived from species compatible with the host cell are used in connection with these hosts.

The vector ordinarily carries a replication site, as well as marking sequences which are capable of providing phenotypic selection in transformed cells. For example, $E. coli$ is typically transformed using pBR 322, a plasmid derived from an $E. coli$ species (Bolivar, et al., $Gene$ 2: 95 (1977)). pBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al, $Nature,$ 275: 615 (1978), Itakura, et al, $Science,$ 198: 1056 (1977); (Goeddel, et al $Nature$ 281: 544 (1979) and a tryptophan (trp) promoter system (Goeddel, et al, $Nucleic\ Acids\ Res.,$ 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors (Siebenlist, et al, $Cell$ 20: 269 (1980)).

In addition to prokaryotes, eukaryotic microbes, such as yeast cultures, may also be used. $Sacchdromyces\ cerevisiae,$ or common baker's yeast is the most commonly used among eukaryotic microorganisms, although a number of other strains are commonly available. For expression in $Saccharomyces,$ the plasmid YRp7, for example, (Stinchcomb, et al, $Nature,$ 282: 39 (1979); Kingsman et al, $Gene,$ 7: 141 (1979); Tschemper, et al, $Gene,$ 10: 157 (1980)) is commonly used. This plasmid already contains the trpl gene which provides a selection marker for a mutant strain of yeast lacking the ability to grow in tryptophan, for example ATCC No. 44076 or PEP4-1 (Jones, $Genetics,$ 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., $J.\ Biol.\ Chem.,$ 255: 2073 (1980)) or other glycolytic enzymes (Hess, et al, $J.\ Adv.\ Enzyme\ Reg.,$ 7: 149 (1968); Holland, et al, $Biochemistry,$ 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture,* Academic Press, Kruse and Patterson, editors (1973)]. Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, *Nature,* 273: 113 (1978) incorporated herein by reference. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provide such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

C. Methods Employed

If cells without formidable cell wall barriers are used as host cells, transfection is carried out by the calcium phosphate precipitation method as described by Graham and Van der Eb, *Virology,* 52: 546 (1978). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F.N. et al *Proc. Natl. Acad. Sci.* (USA), 69: 2110 (1972).

Construction of suitable vectors containing the desired coding and control sequences employ standard ligation techniques. Isolated plasmids or DNA fragments are cleaved, tailored, and religated in the form desired to form the plasmids required.

Cleavage is performed by treating with restriction enzyme (or enzymes) in suitable buffer. In general, about 1 $\mu$g plasmid or DNA fragments is used with about 1 unit of enzyme in about 20 $\mu$l of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.,* 8: 4057 (1980) incorporated herein by reference.

For ligation approximately equimolar amounts of the desired components, suitably end tailored to provide correct matching are treated with about 10 units T4 DNA ligase per 0.5 $\mu$g DNA. (When cleaved vectors are used as components, it may be useful to prevent religation of the cleaved vector by pretreatment with bacterial alkaline phosphatase.)

For analysis to confirm correct sequences in plasmids constructed, the ligation mixtures are used to transform *E. coli* K12 strain 294 (ATCC 31446), and successful transformants selected by ampicillin resistance where appropriate. Plasmids from the transformants are prepared, analyzed by restriction and/or sequenced by the method of Messing, et al, *Nucleic Acids Res.,* 9:309 (1981) or by the method of Maxam, et al, *Methods in Enzymology,* 65:499 (1980).

EXAMPLES

The following examples are intended to illustrate but not to limit the present invention.

Synthesis and Expression of Human IGF-1

Enzymes were obtained from the following suppliers:

New England Biolabs: restriction enzymes, T4 DNA ligase Bethesda Research Labs: restriction enzymes, Bact. Alkaline Phos.

Boehringer-Mannheim: *E. coli* DNA Polymerase I (Klenow) P+L Biochemicals: Polynucleotide kinase, Terminal Nucleotidyl Transferase New England Nuclear:

pBR322 [oligo(dG)-tailed] DNA

Reagents:

BioRad: Bis Acrylamide, Acrylamide, TEMED

Sigma: Ammonium Persulfate

Amersham: 10218 $\gamma^{32}$P ATP>5000 Ci/mmol; 10165 $\alpha^{32}$P dCTP>400 Ci/mmol.

Solutions and Media: 1×TBE: 0.54M Tris Base, 0.54 M Boric

Acid, 0.017 M $Na_2$ EDTA.

Difco: Yeast Nitrogenous Base (YNB); Tryptone, Yeast Extract; Bacto-Agar; Casamino Acids.

Autoradiography:

Kodak X-0 mat AR XAR-2 Film

Glass Beads:

0.45–0.60 mM B. Braun Melsungen AG

LB medium (per liter):

10 g NaCl; 5 g yeast extract; 10 g tryptone; 0.17 ml NaOH (50 percent)

LB Agar (per liter):

10 g tryptone; 5 g yeast extract; 0.5 g NaCl; 15 g Bacto-Agar;

adjusted to pH 7.5 with NaOH.

Antibiotics:

Tetracycline (5 $\mu$g/ml) in all mediums; Ampicillin (20 $\mu$g/ml) in all mediums (plates or liquid)

M9 Medium (per liter):

6 g $Na_2HPO_4$ (anhydrous); 1 g $NH_4Cl$; 3 g $KH_2PO_4$; 0.5 g NaCl; 1 mM $MgSO_4$; 0.5 percent (w/v) glucose; 0.5 percent (w/v) Casamino Acids; 0.0001 percent Thiamine-HCl.

YNB-CAA (per liter):

6.7 g Yeast Nitrogenous Base (without Amino Acids); 10 mg adenine; 10 mg uracil; 5 g Casamino Acids; 20 g Glucose.

YNB-CAA agar plates (per liter):
Same as YNB-CAA +30 g agar.
Standard Ligation Conditions:
10-fold molar excess of insert (or linker) to vector. 1× T4 DNA ligase buffer and 400–800 U T4 DNA ligase; 14°–12–16 hours.
Standard Kination Conditions:
1× Polynucleotide kinase buffer; 15 U polynucleotide kinase;
37°60 minutes; followed by reaction termination by heating to 65° for 10 minutes.
1× Kinase Buffer:
70 mM Tris-HCl (pH 7.6); 10 mM $MgCl_2$; 5 mM DTT
1× T4 DNA Ligase Buffer:
50 mM Tris-HCl (pH 7.8); 10 mM $MgCl_2$; 20 mM DTT; 1 mM rATP.
Construction, Strategy and Selection of a DNA Sequence The 1° protein structure of the human IGF-1 molecule has been determined (1). Based upon this protein sequence and the genetic code, a DNA sequence coding for mature human IGF-1 protein, including all possible base substitutions at any one base position, was determined by computer analysis (Genentech Untrans Program). Using a restriction site analysis program (Genentech Asearch Program), all potential restriction sites located in all possible DNA sequences consistently coding for the same protein were found. Three sites internal to the coding sequence were selected: PstI, BamHI, and AvaII. Two additional sites were placed at the ends, just outside of the coding sequence of the mature protein: one EcoRI site before the initiation codon, AUG, and the SaiII site following the termination codon, TAG of the coding sequence. The choice of these sites facilitated the cloning of the coding sequence in separate parts, each of which subsequently could be excised and then assembled to form an intact synthetic IGF-1 gene. This construction involved the assembly of 4 parts, 2 parts forming the left half, 2 parts forming the right half. Each part consisted of two single strands of chemically synthesized DNA (see FIG. 1). Proposed synthetic fragments were also analyzed for internal complementarity.

The constructions used to generate these four parts employed the use of DNA Polymerase I repair synthesis of synthetic oligonucleotide substrates having 9–10 bp stretches of complementary sequence at their 3' termini. In the presence of DNA Polymerase I (Klenow) and the four deoxynucleoside triphosphates, these primer-templates were extended to become full-length double-stranded DNAs. To prevent priming at locations other than the desired portions as well as self-hybridizations, each set of single-stranded DNAs were analyzed by a computer program (Genentech Homology Program), and wherever possible, sequences which would have potentially led to hairpin loops, self-priming, or mis-priming, were eliminated by alternate codon usage. Each of these four double-stranded DNAs were synthesized to include 9–12 additional bp of non-IGF-1 coding DNA at each end (see FIG. 2). This additional DNA was included to allow generation of sticky ends by restriction enzyme digestion. The sticky ends thus formed facilitated the ligation of the double-stranded pieces to contiguous coding sections of the synthetic gene or into a cloning vehicle.

The 9–12 extra bp of double stranded DNA beyond the restriction site at the end of each part (see FIG. 2) allowed for the TdT-mediated formation of single-stranded oligodeoxycytidine strands at the 3' ends of each double-stranded DNA section. These oligodeoxycytidine tailed double-stranded DNAs could then be annealed into a complementary oligodeoxyguanosine tailed PstI site of a cloning vehicle. Once cloned, and sequenced to ensure the correct base sequences, the parts could be easily isolated and ligated following restriction enzyme cleavage at the restriction sites selected at the ends of each of the four parts, to form the intact synthetic IGF-1 gene.

The method used successfully here was similar to that described by Rossi et al. (28); however, attempts at the construction and cloning of the IGF-1 coding sequence using the Rossi et al. method (28) with only two base pairs of extra DNA beyond the restriction enzyme recognition sites repeatedly failed. The method employed here also differs from the Rossi et al. procedure (28) in that restriction sites placed at both ends of a double stranded DNA allow for the convenience of cloning each double stranded DNA fragment, individually, by (dC)-tailing and annealing into a (dG)-tailed vector, a method which in practice requires less of the double stranded DNA than three-part ligations.

Chemical Synthesis

Eight fragments, 43, 43, 46, 46, 46, 46, 54, and 46 bases in length (see FIG. 1), were chemically synthesized according to the method of Crea and Horn (2), the only change being the use of mesitylene nitrotriazole as the condensing agent rather than 2,4,6-Triisopropyl benzenesulfonylchloride tetrazole.

The syntheses of the fragments were accomplished from the appropriate solid support (cellulose) by sequential addition of the appropriate fully-protected dimer- or trimer-blocks. The cycles were carried out under the same conditions as described in the synthesis of oligothymidilic acid (see Crea et al., supra). The final polymers were treated with base (aqueous conc. $NH_3$) and acid (80 percent HoAc), the polymer pelleted off, and the supernatant was evaporated to dryness. The residue, dissolved in 4 percent aq. $NH_3$, was washed with ethyl ester (3×) and used for the isolation of the fully deprotected fragment.

Purification was accomplished by electrophoresis using 20 percent polyacrylamide gels. The pure oligonucleotide was ethanol precipitated following gel elution.

225–285 pmoles of each chemically synthesized fragment was mixed with an equivalent amount of the complementary single-stranded DNA fragment (i.e. 1L+3L; 2L+4L; 1R+3R; 2R+4R) in the presence of deoxyribonucleoside triphosphates at a final concentration of 200 μM with the exception of dCTP. dCTP was added to a concentration of 5 μM as a $\alpha^{32}$P-labeled isotope (with a specific activity of 1000–2000 Ci/mmol) to allow easy monitoring of the repair-synthesis reaction product. The reactions were carried out in a buffer containing a final concentration of 50 mM Tris HCl pH 7.5; 20 mM $MgCl_2$; 20 mM DTT and 154 DNA Polymerase I (Klenow) in a reaction volume of 200 μl. Reactions were allowed to proceed at 4° for 12–18 hrs.

Upon completion, EDTA was added to a concentration of 25 mM. Sample buffer containing the mixes were phenol extracted, $CHCl_3$ extracted 2×, and products were etOH precipitated. Pellets were taken up in 0.3 M NaOAc and the DNA was reprecipitated with etOH. After dissolving the pellets in $H_2O$, the 1L+3L and 2L+4L products were then digested separately with PstI in 100 μl reaction mixes containing 1×PstI buffer (50 mM $(NH_4)_2SO_4$, 20 mM Tris HCl pH 7.5, 10 mM $MgCl_2$), and 70 U PstI. After 4 hrs, EDTA was added to a concentration of 10 mM, and the material was ethanol precipitated. Pellets were then taken up in 0.3 M NaOAc and reprecipitated, then taken up in $H_2O$. The PstI-digested 1L+3L product was digested with EcoRI at 37° in a 100 μl reaction mix 1×EcoRI buffer (150 mM NaCl, 6 mM Tris HCl pH 7.5, 6 mM MgCl$_2$) and 70 U EcoRI. The PstI digested 2L+4L product was digested at 37° with BamHI in a 100 μl reaction mix in 1×BamHI Buffer (150 mM NaCl, 6 mM Tris HCl pH 7.9, 6 mM MgCl$_2$) and 70 U BamHI. After 4 hrs, EDTA was added to both mixtures, and sample buffer was added. They were electrophoresed on a 6 percent polyacrylamide slab gel. Six percent slab gels were cast with a mixture containing 6 percent (w/v) acrylamide (20 to 1 ratio of acrylamide to Bis acrylamide) 1×TBE, 1 percent APS and 0.1 percent TEMED. Reaction products were located on the gel by autoradiography and the band corresponding to the 45 bp EcoRI-PstI digested 1L+3L product (Part 1) (see FIG. 3) and the band corresponding to the 50 bp PstI-BamHI digested 2L+4L product (Part 2) (see FIG. 3) were excised from the gel, and the material was electroeluted in 0.2×TBE, phenol extracted, CHCl$_3$ extracted, and ethanol precipitated. Parts 1 and 2 were dissolved in H$_2$O.

Cloning Vector Prep

Cloning vector was prepared by digesting 20 μg pBR322 (15) with 50 U EcoRI and 60 U BamHI, in 1×RI Buffer at 37° for 6 hr. After addition of EDTA to a concentration of 10 mM, sample buffer was added, and the mixture was run on a 5 percent polyacrylamide gel. The gel was developed by staining 10' in H$_2$O containing 5 μg/ml Et. Bromide, rinsing 2× in H$_2$O and placing upon a UV transilluminator (302 nM). The band corresponding to the ca. 3712 bp EcoRI-BamHI digested pBR322 molecules was cut from the gel. The DNA was electroeluted from the gel slice, phenol extracted, CHCl$_3$ extracted 2×, and ethanol precipitated. The pellet was dissolved in H$_2$O and was ready for ligation.

Ligation

In a three-part ligation (see FIG. 4), in which the molar ratio of inserts to vector in the ligation reaction was approximately 10 to 1, parts 1 and 2 were ligated into the EcoRI-BamHI digested 322 vector in 1× T4 DNA ligase buffer (cont. 50 mM Tris HCl pH 7.8; 10 mM MgCl$_2$, 20 mM DTT, 1 mM rATP) and ~800 U T4 DNA ligase (NEB). The reaction was carried out at 14° for 12–16 hrs.

Transformations

E. coli strain 294 was used as the transformation host, using the procedure of M. Dagert and S.D. Ehrlich (3). The transformed cells Were plated on LB-agar plates containing ampicillin (20 μg/ml; LB-Amp-plates) and transformants were screened and grown in LB medium containing ampicillin at 20 μg/ml ampicillin. Transformants were screened using a modification of the rapid miniscreen method of Birnboim and Doly (4). Miniprep DNA prepared as such was digested with EcoRI and BamHI and run on polyacrylamide slab gels. Several transformants which illustrated a ca. 218 bp EcoRI-BamHI insert were grown in large scale and plasmids from each were isolated and sequenced according to the procedure of Maxam and Gilbert (5) to confirm the correct chemical synthesis and construction. The pBR322 vector containing the complete correct left half sequence of IGF-1 was called IGF-1 LH 322 (see FIG. 5).

Cloning of Fragments of the Right Half of IGF-1

Figure 6:
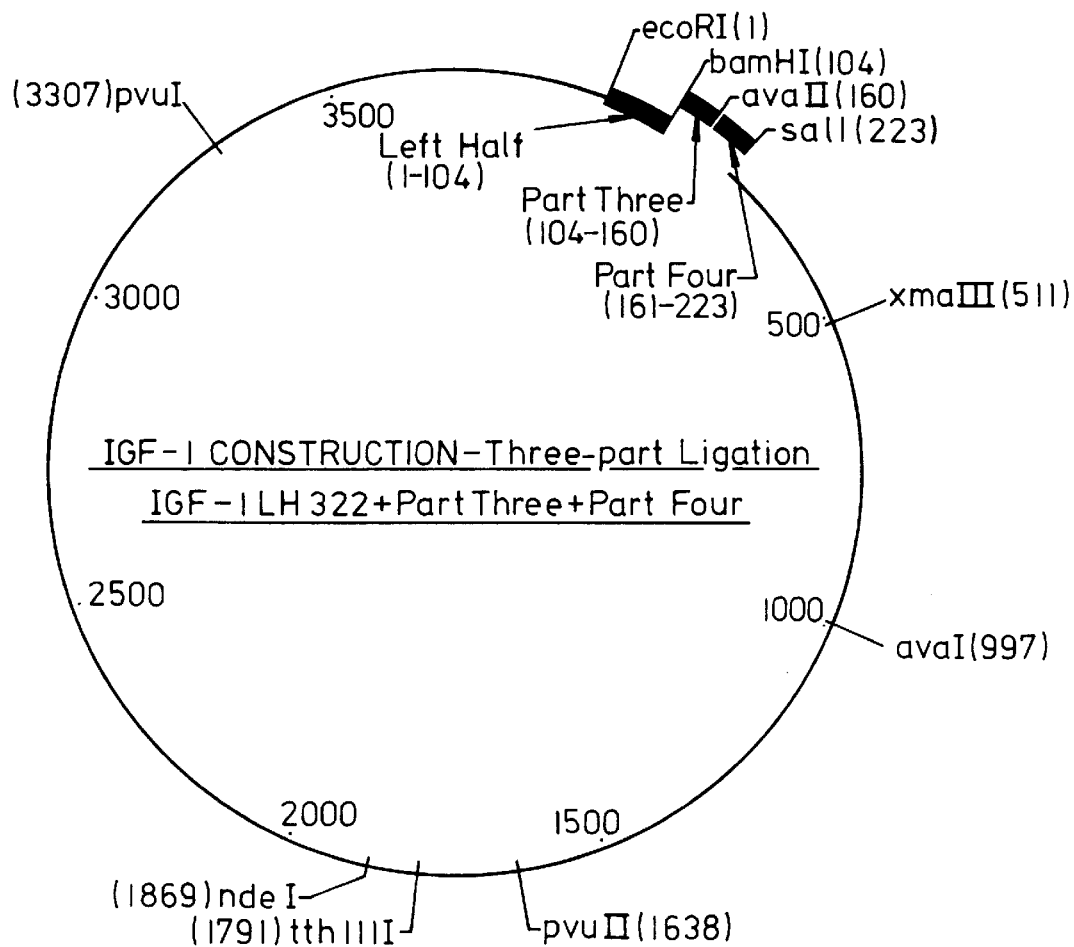
FIG. 6 depicts the ligation of parts 3 and 4 of FIG. 5 into the vector of FIG. 4.

Using the identical conditions of DNA Polymerase I-mediated repair-synthesis, the two pairs of fragments comprising the right half of the synthetic IGF-1 were converted into double-stranded DNAs. After the DNA Polymerase I reactions, and without enzymatic digestion, the 1R+3R (Part III) and 2R+4R (Part IV) reactions were run on a 6 percent polyacrylamide slab gels. The 83 bp (Part III) and 91 bp (Part IV) bands were located by autoradiography and cut from the gel. After electroelution the ethanol precipitated double-stranded DNAs were dC-tailed (see FIG. 6) using the procedures of Villa-Komaroff et al. (6) and Rowenkamp and Firtel (7). Reactions were carried out in 50 μl vols. of 1× tailing mix (cont. 0.2M Pot. Cacodylate, 25 mM Tris HCl pH 6.9, 2 mM DTT, 0.5 mM CoCl$_2$) and 22 μm dCTP. After prewarming at 37° for 10', the 150 second reaction was begun by the addition of 10–20 units of terminal nucleotidyl transferase and terminated by addition of EDTA followed by phenol extraction, CHCl$_3$ extraction 2×, and ethanol precipitation.

These oligo (dC) tailed Parts III and IV were then separately mixed with equimolar amounts of oligo (dG)-tailed PstI cut pBR322 vector in 50 μl of 1× annealing buffer (0.1M NaCl; 10 mM Tris HCl pH 7.8, 1 mM EDTA) at a final DNA concentration of 1–2 μg/ml. After heating to 75° C., the mixes were gradually cooled to 4° over a period of 16 hr and the mix transformed into competent E. coli 294 cells prepared according to the procedure of Dagert and Ehrlich (3). Transformed cells were plated on LB-Tetracycline-Agar plates and grown in LB-Tetracycline medium at tetracycline concentrations of 5 μg/ml. Tetracycline resistant transformants were picked and plated onto LB-Ampicillin-Agar plates to check for insertions at the PstI site. Several tetracycline resistant, Ampicillin-sensitive colonies for each Part 3 and 4 were miniscreened and those exhibiting insertions at the PstI locus were grown in large scale and sequenced by the Maxam and Gilbert technique (5) to confirm the correct DNA sequences of Parts 3 and 4.

Construction of an Intact Synthetic HuIGF-1 Coding Sequence

Preparation: Parts 3 and 4

Parts 3 and 4 Were separately removed from their vectors by digestions of 20 μg of each vector with AvaII in 1× AvaII buffer (60 mM NaCl, 6 mM Tris-HCl (pH 8.0); 10 nM MgCl$_2$; 6 mM 2-mercaptoethanol) and 30 U of AvaII. After 6 hr., at 37°, EDTA was added to the 150 μl reactions to a concentration of 15 mM and the material phenol extracted, CHCl$_3$ extracted 2× and ethanol precipitated. The Part 3 pellet was then taken up in 1×BamHI buffer and digested in a volume of 150 μl with 30 U BamHI at 37° for 4 hr. The pellet containing Part 4 was digested with 30 U SalI in 150 μl of 1×SalI buffer at 37° for 4 hr.

Both digests were then run on 6 percent polyacrylamide slab gels and stained. The 51 bp band representing Part 3 and the 62 bp band representing Part 4 were removed from the gels and the DNA was electroeluted, phenol extracted, CHCl$_3$ extracted 2× and ethanol precipitated. Pellets were then taken up in H$_2$O and were ready for ligation.

Vector Preparation

20 μg of the IGF-1 LH 322 vector was digested with 50 U of BamHI and 50 U of SalI in a 200 μl reaction containing 1×BamHI buffer at 37° for 6 hr. After addition of EDTA to a concentration of 15 mM, the digestion mix was run on a 6 percent polyacrylamide slab gel, ethidium bromide stained and the 3814 bp band excised from the gel.

After electroelution, phenol extraction, chloroform extraction and ethanol precipitation, the DNA pellet was taken up in H$_2$O and was ready for ligation with Parts 3 and 4 in a three-part ligation. The ligation was performed under conditions described above for a three-part ligation (see FIG. 7). Parts 3 and 4 were present in the ligation mix at a 10-fold molar excess of inserts to vector. The mix was transformed into competent E. coli 294 cells prepared according to the Dagert and Ehrlich procedure (3) and plated onto LB-Ampicillin plates. Several transformants were miniscreened and two clones exhibiting a ca. 115 bp BamHI-SalI fragment were grown in large scale and their plasmids prepared. Both strands of the intact synthetic gene were sequenced by the Maxam,-Gilbert technique (5) to confirm the correct sequence. The pBR322 plasmid containing the complete correct sequence coding for Human IGF-1 was called pBR322 HuIGF-1.

Human IGF-1 Expression

IGF-1 Fusion Expression in Bacteria

Initial attempts were to obtain expression of IGF-1 as a fusion protein. To accomplish this, both the pNCV (9) and the pNCVsLE (10) expression vectors were used. (The pNCVsLE expression vector is a derivative of the pNCV vector and was prepared as follows: pNCV was treated with BgII, which cleaves at the 13 codon of the LE fusion. The site was converted to an ECoRI cleavage site using synthetic DNA, to give the expression vector pNCVsLE. The synthetic DNA introduced into the plasmid has the sequence:

5'-GATCCAGAATTC

5' GATCGAATTCTG and this sequence was introduced into the plasmid:

```
GATCCAGAATTC
GTCTTAAGCTAG
```

As a strategy to release the fused human IGF-1 protein from the trp fusion protein, a linker was designed such that an enzymatic proteolysis method reported by Wunsch et al. (8) could be applied to this expression system. To accomplish this, a DNA linker:

```
              ProAla
    5'-AATTCCCTGCCG    -3'
    3'      GGGACGGCCAG-5'
``` was chemically synthesized by standard methods (2) which when linked to the trp fusion protein and the IGF-1 gene, coded for the amino acid residues Proline and Alanine followed by Glycine and Proline which are the first two amino acid residues of IGF-1 and preceded by Proline and Alanine together comprise a recognition site for a collagenase isolated from *Clostridium histolyticum* (11,12). This enzyme reportedly acts at such a site to cleave the alanine-glycine peptide bond.

To construct a DNA sequence coding for a fusion protein with a collagenase cleavage site, 30 μg pBR322 HuIGF-1 plasmid was cleaved with 50 U BamHI and 50 U PvuI enzyme in 200 μl 1×BamHI buffer at 37° for 6 hours. After addition of EDTA to a concentration of 15 mM, the reaction mix was chromatographed on a 6 percent polyacrylamide slab gel. The smaller PvuI-BamHI fragment (~725 bp) was isolated and digested with 40 U AvaII in 150 μl 1×Sau96I buffer (60 mM NaCl, 6 mM Tris-HCl pH 7.4, 15 mM $MgCl_2$, 6 mM 2-mercaptoethanol). After addition of EDTA to a concentration of 15 mM, the resulting mix chromatographed on a 6 percent polyacrylamide slab gel. The smaller Sau96I-BamHI fragment (~86 bp) was extracted from the gel, phenol extracted, chloroform extracted 2×, and ethanol precipitated. This fragment was ready for ligation.

200 pmols of linker fragments were kinased with 100 U polynucleotide kinase in 20 μl of 1× polynucleotide kinase buffer (70 mM Tris-HCl (pH 7.6); 10 mM $MgCl_2$; 5 mM DTT; 1 mM rATP) at 37° for 1 hour. The reaction was terminated by heating to 65° C. for 5 minutes. 100 pmols of the kinased linker fragments were ligated to the 86 bp Sau96I-BamHI fragment with 400 U of T4 DNA ligase in 30 μl of 1× T4 DNA ligase buffer at 14° for 12–16 hours. The ligation reaction was terminated by addition of EDTA to a concentration of 15 mM followed by phenol extraction, chloroform extraction 2×, and ethanol precipitation. The pellet was then taken up in 1×BamHI buffer and digested in a 100 μl reaction with 50 U of EcoRI and 50 U of BamHI at 37° for 6 hrs. After terminating the digestion with EDTA, the mixture was chromatographed on a 6 percent polyacrylamide slab gel and the newly created (~97 bp) EcoRI-BamHI fragment was extracted from the gel, and prepared for ligation. The vector to receive this new fragment was prepared by digesting 30 μg pBR322 HuIGF-1 with 100 U of each EcoRI and BamHI in 200 μl of 1×BamHI buffer at 37° for 8 hr. The reaction was terminated, chromatographed on a 6 percent polyacrylamide slab gel and the larger band (~3830 bp) representing the EcoRI-BamHI digested plasmid was isolated and the plasmid DNA extracted and prepared for ligation as above. In a 30 μl ligation reaction containing a 10-fold molar excess of insert fragment to vector, the EcoRI-BamHI fragment was ligated into the EcoRI-BamHI digested plasmid pBR322 HuIGF-1 under standard ligation conditions mentioned above. Competent *E. coli* 294, prepared as above (3), were used as transformation hosts and the transformed cells were plated onto LB-Ampicillin agar plates. Several transformants were picked, miniscreened as above (4), and two exhibiting an EcoRI-BamHI insertion were grown in large scale and their plasmids purified. Using the Maxam-Gilbert procedure (5) the construction was sequenced to verify the correct synthesis and insertion of the EcoRI-Sau96I collagenase linker. This plasmid Was called pBR322 HuSynIGF-1-M.

To prepare this EcoRI-SalI IGF-1 coding sequence for insertion into pNCV and pNCVsLE, 30 μg of pBR322 HuSynIGF-1-M was digested with 70 U of SalI in 200 μl of 1×SalI buffer (150 mM NaCl, 6 mM Tris-HCl (pH 7.9); 6 mM $MgCl_2$; 6 mM 2-mercaptoethanol) at 37° for 6 hours. After addition of EDTA to 15 mM, the mixture was phenol extracted, chloroform extracted 2×, and ethanol precipitated.

Using standard chemical synthesis procedures (2) a SalI-EcoRI linker

```
    5' TCGACGTACATG      3'
    3'     GCATGTACTTAA  5'
``` was synthesized and 400 pmols kinased, as above. 200 pmols of the kinased linker was ligated to the SalI digested pBR322 HuSynIGF-1-M (prepared above) with 800 U T4 DNA ligase in 30 μl of 1× ligation buffer for 12–16 hours at 14° C.

After termination of the reaction with EDTA, the mixture was phenol extracted, chloroform extracted 2×, and ethanol precipitated. The pellet was then taken up in 1×EcoRI buffer and digested with 100 U EcoRI in a volume of 200 μl for 8 hours at 37°. After addition of EDTA to a concentration of 15 mM, the mixture was chromatographed on a 6 percent polyacrylamide slab gel. The gel was stained and the ~230 bp band corresponding to the EcoRI-EcoRI HuIGF-1 fragment was extracted from the gel, phenol extracted, chloroform extracted 2×, and ethanol precipitated. This fragment was ready for ligation into pNCV and pNCVsLE. pNCV and pNCVsLE were prepared for ligation by digestion of 20 μg of each with 100 U EcoRI in 200 μl 1×EcoRI buffer at 37° for 8 hours. After digestion, 200 U of bacterial alkaline phosphatase was added to each reaction and the mixtures were warmed to 65° C. for 2 hours. EDTA was added to a concentration of 15 mM and the mixes were phenol extracted 3×, chloroform extracted 2× and then ethanol precipitated. These expression vectors were prepared for ligation.

Ligations of the EcoRI-EcoRI Human IGF-1 fragment into the two expression vectors were performed in 30 μl reaction volumes in 1× T4 DNA ligase buffer with 800 U T4 DNA ligase at 14° for 12–16 hours. The EcoRI-EcoRI fragment was present at a 10-fold molar excess to vector.

Competent *E. coli* 294 were prepared (3) (ATCC 31446) and used as transformation hosts for the ligations. Transformed cells were plated onto LB-agar plates containing tetracycline (5 µg/ml; LB-Tet-plates) and transformants were miniscreened (4). Miniscreen plasmid DNA from transformants of the pNCV-IGF-1 construction were digested with both PstI and BGlII to determine the orientation of the EcoRI fragment insertions. Two clones whose plasmids contained a ~570 bp BglII-PstI fragment (as opposed to a ~690 bp fragment) were grown in large scale and their plasmids prepared. The construction was sequenced using the Maxam-Gilbert procedure (5) to confirm the correct insertion at the junction of the trp fusion and IGF-1 protein coding sequences as well as retention of the desired reading frame. Plasmids with the correctly inserted IGF-1 fragment were called pNCVLE-IGF-1. Transformants of the pNCV-sLE-IGF-1 construction were also miniscreened by the same procedure (5), and the plasmid DNAs were digested with HincII and PstI. Two clones exhibiting a ~150 bp HincII-PstI fragment (as opposed to a ~105 bp HincII-HincII fragment) were grown in large scale and their plasmids prepared. Using the Maxam-Gilbert techniques (5), the functions of the trp fusion and IGF-1 protein coding sequences were sequenced to ascertain proper orientation and retention of the proper reading frame. Those plasmids possessing the correct insertion and proper reading frame were called pNCV-sLE-IGF-1.

To attempt expression of each of these constructions, two clones, one possessing pNCV-IGF-1 and the other possessing pNCV-sLE-IGF-1, were inoculated into 10 ml M9-Tetracycline culture medium supplemented with 0.5 mg/ml Tryptophan. A clone containing pNCV-LE with no IGF-1 gene insert was also inoculated into culture medium to provide as a negative control in assays.

After 12–16 hours growth at 37° with agitation, 0.5 ml of these cultures were used to inoculate 250 milliliters of M9-Tetracycline culture medium. After growing for 12–16 hours at 37° with agitation, the cells were harvested by centrifugation at 5000 rpm for 10 minutes in a Sorvall GSA rotor. The refractile bodies were purified from the pelleted cells by: a) suspending the host cells in a buffered solution of ionic strength suitable to solubilize most of the host protein, b) subjecting the suspension to cell wall/membrane disruption, c) centrifuging the disrupted suspension at low speed to form a pellet, optionally repeating the foregoing steps, and d) recovering the heterologous protein as refractile bodies in the pellet (Reference 13). A small quantity of refractile particles of each of the three preparations was boiled in SDS and 2-mercaptoethanol containing sample buffer and run on SDS-polyacrylamide slab gels according to the Laemmli method (14). The size of the protein expressed by pNCV-IGF-1 (LE-IGF-1) was ~28,670 Daltons (see FIG. 7), and ~9770 Daltons for the pNCV-sLE-IGF-1 protein (sLE-IGF-1) (see FIG. 8). These two expressed proteins were subjected to solubilization in 6M Guanidine-HCl followed by 50-fold dilution with dilute buffers. The final buffer for pNCV-IGF-1 after dilution was 0.12 M Guanidine-HCl; 0.05 M 7922 Tris-HCl pH 8, 20 percent glycerol; 0.1 mg/ml BSA; 0.15 M NaCl; 0.1 mM EDTA and the final buffer after dilution of the pNCV-sLE-IGF-1 refractile bodies was 0.14 M Guanidine-HCl; 25 mM Tris-HCl pH 7.6; 10 mM $CaCl_2$. After spinning out particulate matter, the two solutions containing solubilized trp-IGF-1 fusion proteins were assayed by a radioimmune assay procedure of Furlanetto et al. (23), as modified by Hintz et al. (24). Both fusion proteins demonstrated activity in this assay. A negative control prep was also included in the assay and the control exhibited no measurable activity.

Expression and Secretion in Yeast

To avoid the necessity of refractile body purification and solubilization, from bacterial cell lysates, yeast expression-secretion systems were sought as an alternative. Aside from the advantage of avoiding protein purification from cell lysates, coupled expression-secretion systems might obviate a subsequent in vitro processing step to remove a fused protein. Available were three yeast expression-secretion systems. These were: 1) yeast α factor (22), employing yeast α-factor promoter and preprosequence; 2) yeast invertase (16) consisting of the invertase promoter and signal sequence; and 3) a hybrid, composed of the PGK promoter (25) and invertase signal (16).

Yeast Alpha-Factor Promoter Pre-Alpha Factor IGF-1 Plasmid Construction

Figure 9:
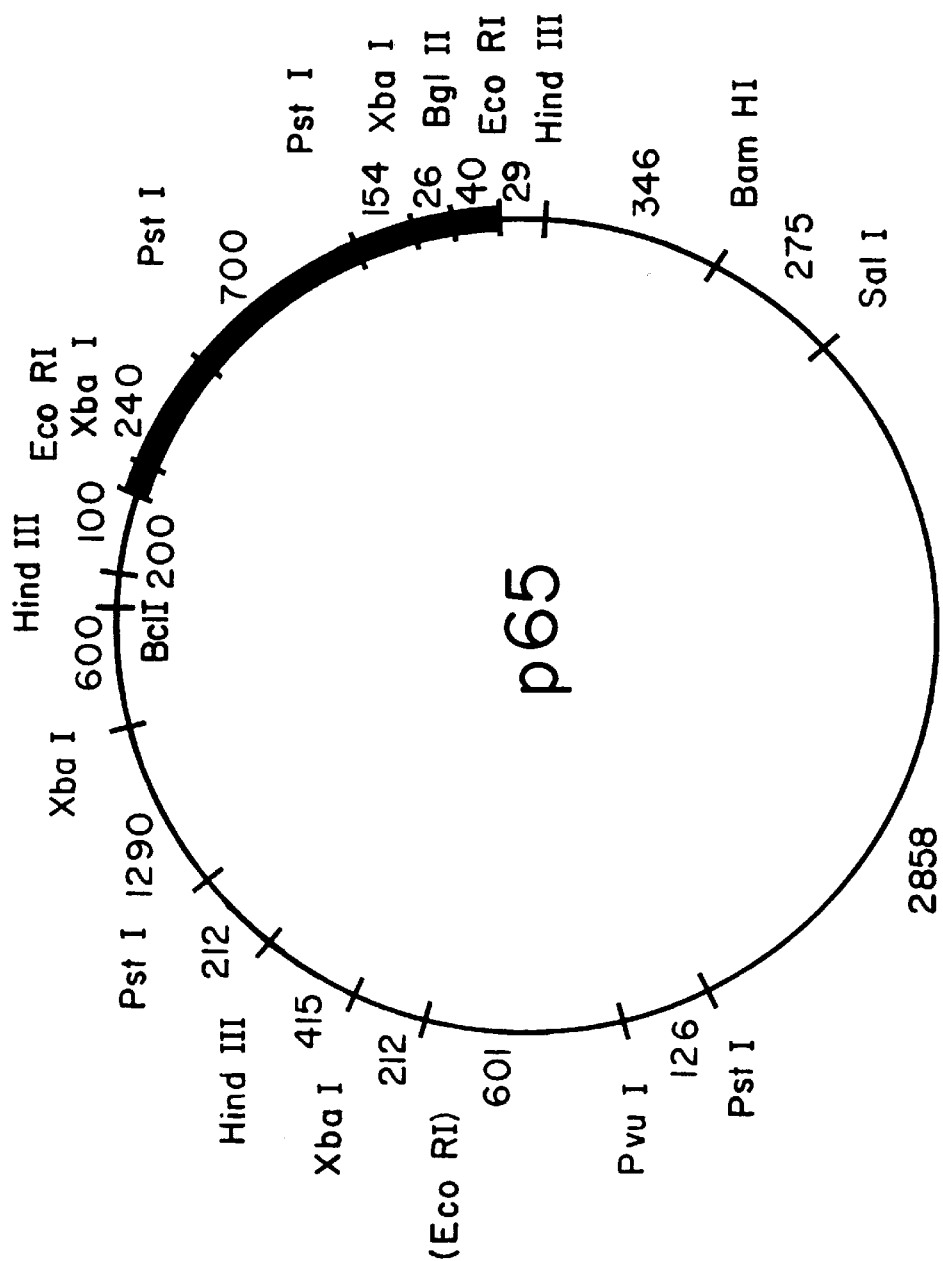
FIG. 9 depicts a plasmid used in the present construction.

To obtain expression of IGF-1 using the a factor promoter and preprosequence, a plasmid constructed by Singh (22) was used. Plasmid P65 (FIG. 9) possesses sequences of the α-factor promoter, α-factor preprosequence, yeast 2 micron terminator, the yeast Trp 1 gene, as well as portions of the pBR322 plasmid. Plasmid p65 was obtained by its following method: The 15-mer oligonucleotide probes for the α-factor gene were designed on the basis of the amino acid sequence of the pheromone (23a) and yeast codon usage frequencies. The rationale is outlined in FIG. 19 where the last 5 amino acids of the α-factor and all the possible codons and their usage frequencies are given. (The codon usage is the total of 2 different glyceraldehyde-3-phosphate dehydrogenase clones (23b, 23c) and of alcohol dehydrogenase I.) The codon usage for these and other genes has recently been summarized identical, to the MFα1. The α-factor encoded by this gene is apparently made as a precursor protein of 120 amino acid residues containing two copies of the pheromone. One of the α-pheromone tridecapeptides contained in the putative precursor is identical to the pheromone copies encoded by the MFα1 gene, whereas the second copy contains a Gln→Asn and a Lys→Arg.

Figure 24:
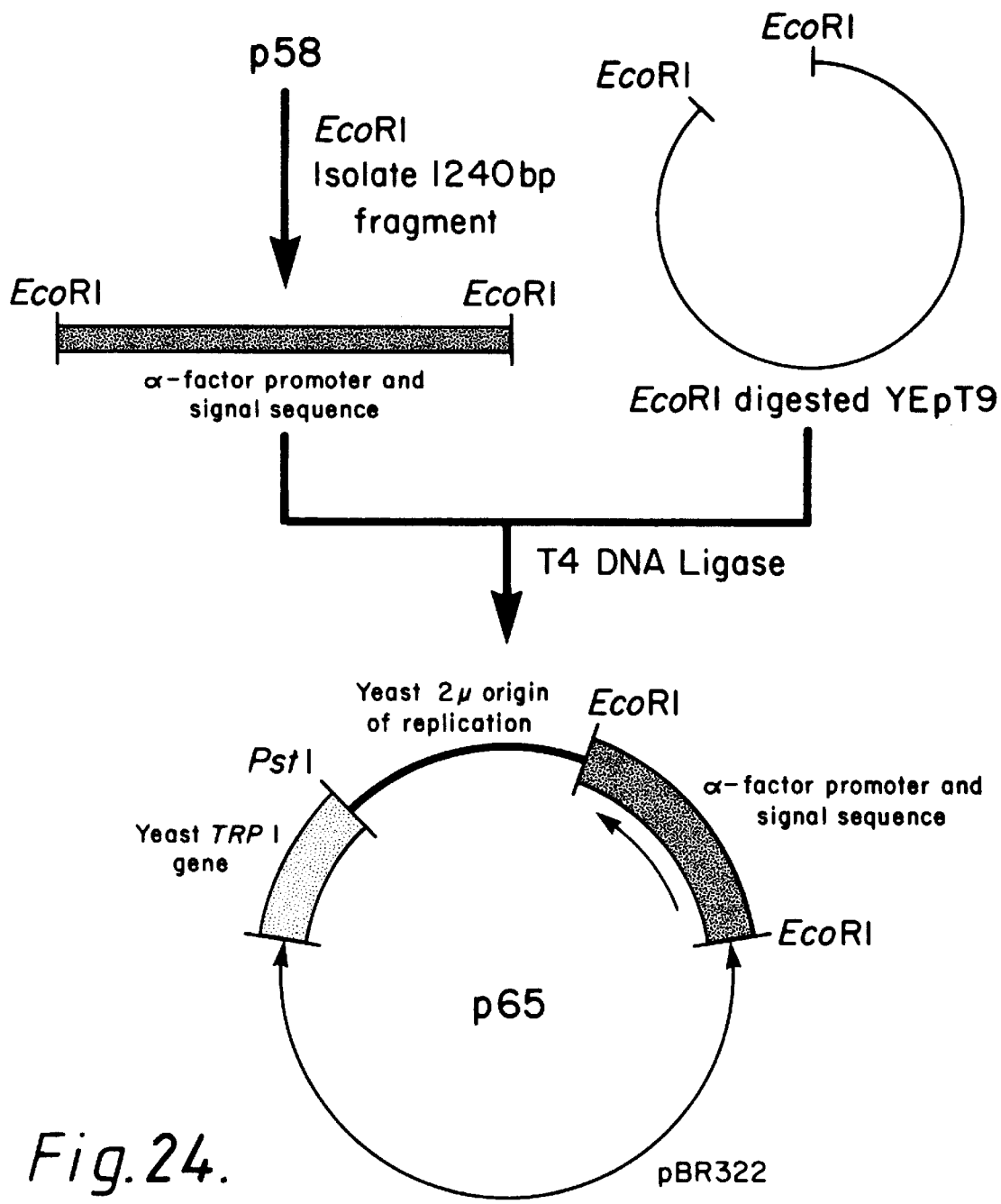
FIG. 24 illustrates the scheme for construction of a yeast/*E. coli* shuttle vector for use as a starting plasmid herein for expression of heterologous genes supplying the α-factor promoter and signal polypeptide gene sequences.

E. Construction of a Plasmid p65 for Expression and Secretion of Human Interferon The preparation of a plasmid to demonstrate the usefulness of the α-factor promoter and the α-factor presequences for expression and secretion of heterologous gene products is outlined in FIGS. 23–24. The DNA sequences coding for the α-factor peptides were removed from one of the α-factor clones (p53) such that the resulting plasmid, p57, contained the promoter sequences and the sequence corresponding to 89 amino acids of the α-factor "prepro" protein. This sequence was then joined with human interferon D (IFN-$α_1$) gene to form plasmid p58. For this purpose an expression plasmid p65 was constructed as shown in FIG. 24. This plasmid, like YEp9T, contains the origins of replication for *E. coli* and yeast as well as selective markers for selection in each of these two organisms. It also contains a convenient EcoR1 site for gene insertion so that any gene that is contained on an EcoRI fragment where the first codon of the gene is immediately preceded by the EcoRI site could be tested for the synthesis and secretion of the corresponding protein. Due to the dearth of convenient restriction sites in the α-factor preprosequence, to insert the IGF-1 coding sequence, the identical ~230 bp EcoRI-EcoRI HuSynIGF-1-M fragment that was ligated into pNCV and pNCVsLE (as mentioned previously in bacterial construction) was used. This EcoRI-EcoRI fragment contained the collagenase recognition site Proline-Alanine-Glycine-Proline, and allowed for collagenase digestion should IGF-1 be secreted as a fusion protein. The protein expressed in this construction (see FIG. 10) consists of the prepro α-factor protein fused to IGF-1.

To insert the ~230 bp EcoRI-EcoRI fragment, the plasmid P65 was partially digested in 1×EcoRI buffer with EcoRI, and then sized upon a 0.7 percent horizontal agarose gel. The band corresponding to the linearized singularly restricted plasmid was excised, eluted from the gel, and phenol extracted, chloroform extracted 2×, and then ethanol precipitated. This DNA pellet was then taken up in 50 mM Tris-HCl (pH 8) and treated with bacterial alkaline phosphatase under conditions to ensure 100 percent dephosphorylation of the 5' protruding ends. Following this treatment, the phosphatase activity was removed by first adding EDTA to a concentration of 15 mM, then extracting the DNA with phenol 3×, chloroform extracting 2×, and ethanol precipitating the vector. This material then contained linearized P65 vector, digested with EcoRI in either of two locations: one, either at the EcoRI site upstream of the α-factor promoter and preprosequence, or at another, at the EcoRI site just downstream of the α-factor promoter and preprosequence. The ~230 bp EcoRI-EcoRI IGF-1 fragment was ligated into the vector. The desired location of insertion was at the EcoRI site just downstream from the α-factor promoter and preprosequence.

Figure 11:
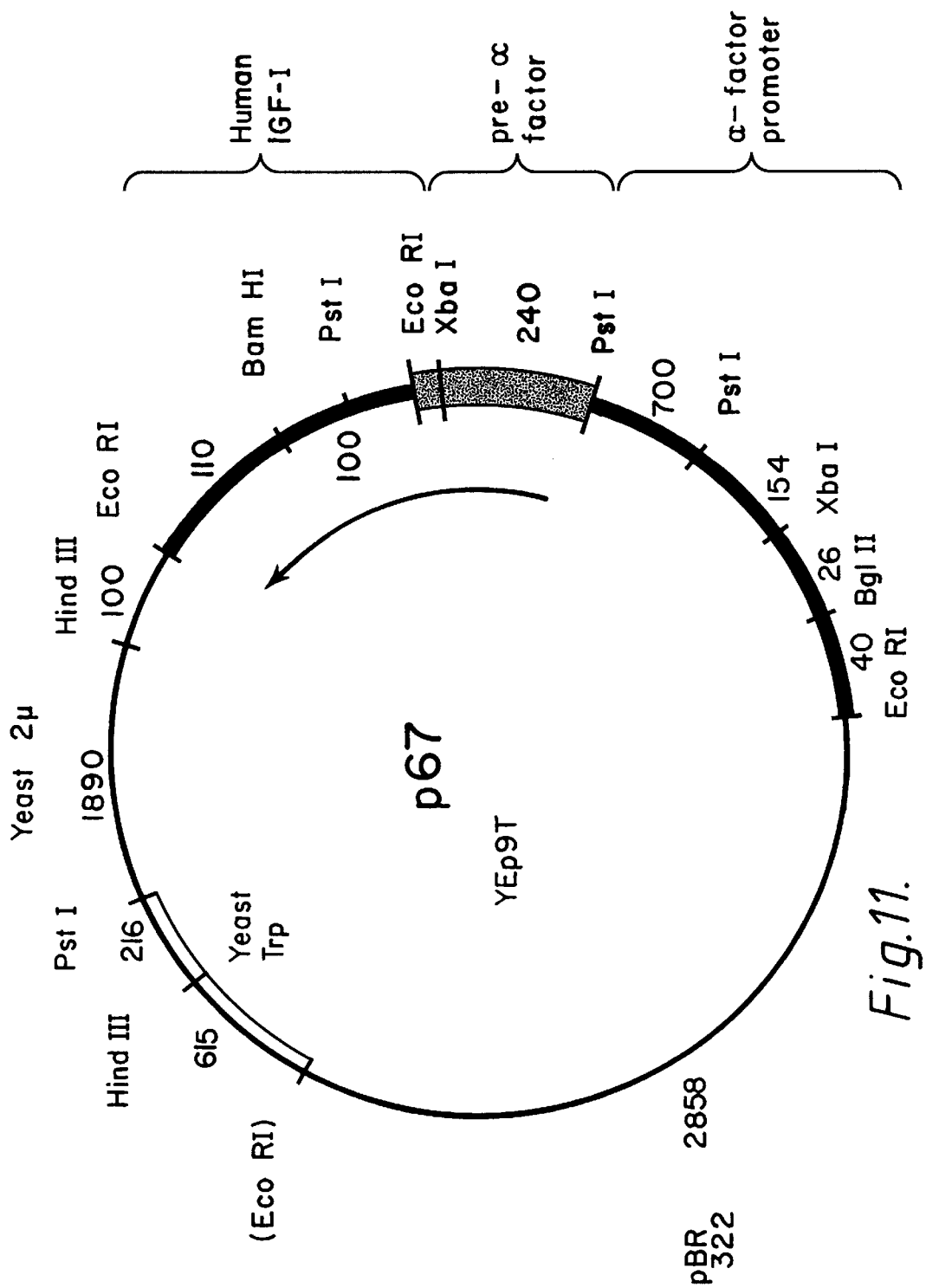
FIG. 11 is a vector containing alpha factor promotor and pre-pro sequence fused to IGF-I.

The ligation was carried out under standard ligation conditions and the transformation hosts were competent *E. coli* 294 prepared according to Dagert and Ehrlich (3). The transformed cells were plated onto LB-Amp-Agar plates. Several transformants were miniscreened according to the method of Birnboim and Doly (4), and plasmid DNA prepared as such was digested with both SalI and HindIII in the appropriate buffers. One of several clones which contained a plasmid with an ~110 bp EcoRI-HindIII fragment was grown in large scale and its plasmid was purified. This plasmid, YEp9T α-factor EcoRI-EcoRI IGF-1 (see FIG. 11), was used to transform competent yeast strain 20B-12 (αtrp pep4) cells according to the Hitzeman modification (19) of Hinnen et al. (17) and Beggs et al. (18) procedures.

Two such transformants, as well as a negative control transformant (with no IGF-1 insertion in the plasmid), were grown in suspension as were those of the yeast pre-invertase-IGF-1 plasmid transformations. Supernates were tested for secreted IGF-1 activity, as measured by the radioimmune assay procedure of Furlanetto et al. (23) as modified by Hintz et al. (24). Both supernates of transformants having plasmids with IGF-1 inserts contained IGF-1 activity and the negative control supernate did not. One of these transformants was grown in large scale in a 10 liter fermenter and the supernate contained secreted IGF-1 activity at a peak level of ~3 µg/ml. The IGF-1 activity of the fermentation supernate was also demonstrated by a placental membrane radioreceptor assay developed by Horner et al. (26).

Yeast Invertase Promoter Signal IGF-1 Plasmid Construction

Based upon evidence of correct processing and secretion in yeast of proteins with heterologous signal sequences (16), the yeast invertase expression-secretion system became of interest. Attempted first was expression of the yeast invertase signal protein fused to IGF-1 (FIG. 12), coupled with the processing and secretion of IGF-1, using the invertase promoter as a starting point for transcription.

The yeast invertase signal coding sequence was attached to the IGF-1 gene by the use of a NcoI-HindIII (~400 bp) fragment containing the initiation ATG codon and 5' end of the signal DNA sequence, and 4 DNA fragments synthesized by standard procedures (2):

The construction began with the isolation of the 90 bp AvaII-BamHI IGF-1 left half fragment by AvaII digestion of a ~730 bp PvuI-BamHI fragment isolated from PvuI-BamHI digested pBR322-HuSynIGF-1.

After phosphorylation of all four synthetic DNA fragments using standard kination conditions, the four synthetic fragments were mixed with the AvaII-BamHI IGF-1 left half fragment and ligated using standard ligation conditions. Following inactivation of the ligase by phenol and chloroform extraction 2×, the ethanol precipitated DNA pellet was dissolved and digested with HindIII and BamHI in the appropriate buffers. Newly constructed HindIII-BamHI (ca. 140 bp) fragment was isolated and extracted from a 6 percent polyacrylamide gel. This material was then ligated into HindIII-BamHI digested pBR322 vector, which had been first digested with HindIII, then BamHI in the appropriate buffers, followed by purification of the 4014 bp vector fragment from a 6 percent gel.

The transformation host was competent *E. coli* 294 prepared by standard procedures (3) and the transformed cells were plated onto LB-Ampicillin agar plates. Several transformants were miniscreened by the Birnboim-Doly procedure (4) and their plasmid DNAs digested with EcoRI and BamHI. Two plasmids containing a ~167 bp EcoRI-BamHI fragment (illustrating the insertion of a 140 bp fragment into the HindIII and BamHI sites) were grown in large scale and their plasmids prepared. Using Maxam-Gilbert sequencing techniques (5), the entire 43 bp HindIII-AvaII section of DNA was sequenced to confirm the correct chemical synthesis and construction. The correctly constructed plasmid was called pBR322-P-I-HuSynIGF HindIII-BamHI (~4154 bp).

To insert the right half of the IGF-1 gene, this newly created plasmid was digested with BamHI-SalI in the appropriate buffers and the larger fragment (~3879 bp) was purified by gel fractionation. pBR322 HuSynIGF was digested with BamHI-SalI in the appropriate buffers and the 115 bp BamHI-SalI fragment corresponding to the right half of the IGF-1 gene was isolated by gel fractionation. This 115 bp BamHI-SalI IGF-1 right half fragment was then ligated into the BamHI-SalI digested pBR322-P-I-IGF-1 LH HindIII-BamHI vector using standard ligation conditions. Competent *E. coli* strain 294 prepared according to Dagert and Ehrlich (3) were used as transformation hosts and transformed cells were plated onto LB-Amp-Agar plates. Several transformants were miniscreened using standard techniques (4) and plasmid DNA prepared as such was digested with EcoRI and SalI in the appropriate buffers and those plasmids illustrating an insertion of the BamHI-SalI fragment corresponding to the right half of IGF-1 were called pBR322 P-I-HuSynIGF-1 HindIII-SalI. One of the clones containing the pBR322 P-I-IGF-1 HindIII-SalI plasmid was grown in large scale and the plasmid was isolated. This plasmid was then digested with HindIII and SalI in the appropriate buffer to prepare a 255 bp HindIII-SalI fragment containing all of the IGF-1 gene and the 3' portion of the yeast invertase signal coding sequence. This fragment of DNA was isolated by polyacrylamide gel fractionation and prepared for ligation by standard techniques. The (~400 bp) NcoI-HindIII fragment containing the 5' end of the DNA sequence coding for the invertase signal as well as the yeast invertase promoter was created by NcoI and HindIII digestion of plasmid YIpsp-LeIFA (16) in the appropriate buffers. The YIpsp-LeIFA plasmid was first digested with NcoI to completion in the appropriate buffer, then phenol extracted, chloroform extracted 2× and ethanol precipitated. The linearized molecules were then taken up in 1×HindIII buffer and partially digested to generate the needed NcoI-HindIII (~400 bp) fragment which contains an internal HindIII restriction site. This NcoI-HindIII fragment was then isolated by gel fractionation and prepared for ligation using standard techniques. To provide for a vector, plasmid pUC12-YI (EcoRI-BamHI) (designated p4.3 kb in citation 16) was digested with NcoI and SalI in the appropriate buffers. After purification by gel fractionation, the ~2.6 kbp vector was eluted from the gel and prepared for ligation by standard techniques. To perform the final construction, a three-part ligation was arranged using standard ligation techniques. The DNA used in the ligation included the NcoI-SalI-digested pUC12-YI (EcoRI-BamHI) (16), the ~400 bp NcoI-HindIII and the ~255 bp HindIII-SalI fragments. After ligation, the material was transformed into competent E. coli 294 cells prepared according to Dagert et al. (3). Transformed cells were plated onto LB-Amp-Agar plates and several transformants were miniscreened using the procedure of Birnboim and Doly (4). Plasmid DNA prepared as such was digested with NcoI and SalI in the appropriate buffers and one of several clones containing plasmids exhibiting the insertion of a ~625 bp NcoI-SalI DNA fragment was grown in large scale and its plasmid was purified.

As a final step, this plasmid was linearized by digestion with SalI in the appropriate buffer. SalI-EcoRI linker, prepared as mentioned above, and kinased under standard kination conditions, was ligated to the linearized vector to convert the SalI ends to EcoRI ends using standard ligation conditions. After termination of the ligation reaction by addition of EDTA to 15 mM, phenol extraction, chloroform extraction 2× and ethanol precipitation, the DNA pellet was dissolved in 1×EcoRI buffer, and digested with EcoRI. The EcoRI digestion released a ~1150 bp EcoRI fragment which contained the yeast invertase promoter, yeast invertase signal coding sequence and the IGF-1 coding sequence in one contiguous sequence. This material was isolated as a ~1150 bp band from a 6 percent polyacrylamide slab gel after fractionation and prepared for ligation using standard procedures.

The yeast-E. coli shuttle vector to receive this EcoRI fragment was prepared by EcoRI digestion of plasmid YEp9T (16) to-linearize the vector, followed by treatment of the EcoRI termini with bacterial alkaline phosphatase using conditions recommended by the manufacturer to produce 100 percent dephosphorylation of the 5' protruding ends. The phosphatase reaction was terminated by addition of EDTA to 15 mM and the mixture phenol extracted 3×, chloroform extracted 2×, and then the DNA was ethanol precipitated. After redissolving the DNA pellet in 1× ligation buffer, the vector was mixed with the EcoRI ~1150 bp fragment and ligated under standard ligation conditions. Competent E. coli 294 cells prepared according to Dagert et al. (3) were used as transformation hosts and the transformants were plated onto LB-Amp-Agar plates. To determine the orientation of the insertion, several transformants were miniscreened using the method of Birnboim and Doly (4) and plasmid DNAs purified as such were digested with BamHI in the appropriate buffer. One of several transformants possessing plasmids which produced a 1.3 kb BamHI-BamHI fragment upon BamHI digestion (as opposed to a ~475 bp fragment) was grown in large scale and its plasmid was purified. This plasmid, called P.I.IGF-1 EcoRI-EcoRI P.I. Promoter was used to transform competent yeast cells prepared essentially according to the methods of Hinnen, A., et al. (17), and Beggs, J.D. (18), but with the modifications of Hitzeman (19). The yeast strain 20B-12 (αtrp1 pep4) was used and was obtained from the Yeast Genetics Stock Center. In this construction, the expression of IGF-1 begins With transcription at the invertase promoter and terminates in the yeast 2 micron sequence. The fusion protein expressed by this construction consisted of the yeast invertase signal fused to the IGF-1 protein, the combined molecular weight of which was 9964 Daltons. Another plasmid with the EcoRI fragment inserted in the reverse orientation was also used to transform competent yeast cells. In this construction, the IGF-1 was not provided with the yeast terminator.

Several transformants were picked and streaked on YNB-CAA agar plates. Among these, three transformants were picked and inoculated into 10 ml of YN3-CAA grow-up medium, in shake flasks. A fourth culture was also started using a colony transformed with the same vector, but with the EcoRI fragment inserted into the vector in the reverse orientation. After 16–20 hours growth at 30°, the cultures were sampled (1 ml) and cleared of cells by spinning 5' in an eppendorf microfuge. Supernatants were taken off and assayed for secreted activity using the radioimmune assay procedure of Furlanetto et al. (23) as modified by Hintz et al. (24). The supernates of the three transformants demonstrated activities of 1.7 to 3.3 ng/ml of IGF-1 activity and the negative control showed no activity. To determine intracellular activity, the pellets from 1 ml of culture were washed 1× in 25 mM Tris-HCl (pH 7.6), 1 mM EDTA and then lysed by 3–4 minutes of vigorous vortexing in 0.5 ml of the above Tris-EDTA solution with 0.4 ml of glass beads.

Assay of the cell lysates demonstrated IGF-1 activities of 1.5–2.8 ng/ml in the three IGF-1 secreting transformants and no activity in the negative control transformant. The highest secretor of the three transformants was grown in a 5 liter fermentation and the secreted IGF-1 activity reached a peak of 74 ng/ml of supernate.

Yeast PGK Promoter Pre-Invertase IGF-1 Plasmid Construction

One difficulty in the use of the invertase promoter was that it was subject to repression in the presence of glucose. Due to the incompatibility of glucose with high levels of transcription initiation at the invertase promoter, the PGK promoter was sought as an alternative promoter, glucose, being the mainstay carbon source of fermentation processes.

To begin construction of the PGK promoter P.I.IGF-1 construction, it was necessary to clone a fragment containing the entire invertase signal coding sequence. To do this, plasmid pLeIF-A-Invertase Signal (16) was digested with BglII and then BamHI in the appropriate buffers. This digestion released several fragments, one of which was a ~625 bp BglII-BamHI fragment which was isolated from a 6 percent polyacrylamide slab gel and prepared for ligation using standard techniques. To clone this fragment, the pUC8 vector was chosen as a cloning vehicle. pUC8 plasmid was digested with BamHI in 1×BamHI buffer, treated with bacterial alkaline phosphatase to dephosphorylate the 5' termini, and then run onto and purified from a 5 percent polyacrylamide slab gel.

After standard preparation for ligation the BamHI digested vector was mixed with the above ~625 bp BglII- BamHI fragment, and ligated under typical ligation conditions. The mixture was then transformed into competent *E. coli* 294 prepared by the Dagert et al. method (3) and the transformed culture plated onto LB-Amp-Agar plates. Several transformants were picked and miniscreened using the Birnboim and Doly (4) technique. Miniscreen plasmid DNA was digested with EcoRI and an analytical gel of the digests illustrated two types of plasmids having EcoRI fragments either ~260 bp or ~385 bp in length. One clone containing a ~260 bp EcoRI fragment was grown in large scale and its plasmid purified. This plasmid was called pUC8 P.I. Promotor-Signal BglII-BamHI.

A clone of this type was chosen because of the desired orientation of the inserted BglII-BamHI fragment. What was needed from this plasmid was an ~20 bp EcoRI-HindIII fragment containing the ATG initiation codon and 5' end of the invertase signal coding sequence.

To construct the intact invertase signal coding DNA sequence, ~150 bp HindIII-BamHI fragment containing the 3' end of the signal sequence fused to the left half of the IGF-1 gene was isolated from HindIII-BamHI digestion of plasmid pBR322 P.I. IGF-LH HindIII-BamHI (~4154 bp). Isolation was by polyacrylamide slab gel fractionation, and the DNA band corresponding to the ~150 bp fragment was excised and prepared for ligation using standard techniques.

To obtain the short (~20 bp) EcoRI-HindIII fragment, the plasmid pUC8 P.I. Promotor-Signal-BglII-BamHI was digested with EcoRI in 1×EcoRI buffer. This digestion released the ~260 bp EcoRI-EcoRI fragment which was isolated from a 6 percent polyacrylamide slab gel after fractionation of the digestion mixture. This ~260 bp fragment was then digested with HindIII in the appropriate buffer, causing the creation of two. HindIII-EcoRI fragments, one ~20 bp and the other ~240 bp in length. After complete digestion, the digestion was terminated by addition of EDTA to 15 mM and the entire mix phenol extracted, chloroform extracted 2×, and then ethanol precipitated.

A vector was prepared by EcoRI-BamHI digestion of pBR322 (15) in the appropriate buffers followed by purification of the EcoRI-BamHI digested vector from a 5 percent polyacrylamide slab gel. After preparation for ligation using standard techniques, the vector was mixed with the ~150 bp HindIII-BamHI fragment (3' end of invertase signal +Left Half IGF-1), and the two HindIII-EcoRI fragments (the ~20 bp fragment containing the 5' end of the invertase signal coding sequence), and the entire mixture was ligated under standard ligation conditions. Competent *E. coli* 294 prepared according to Dagert and Ehrlich (3) were used as transformation hosts for the ligation, and the transformed cells plated onto LB-Amp-Agar plates. Several transformants were miniscreened according to Birnboim and Doly (4) and the purified miniscreen DNAs were digested with EcoRI and BamHI. One of several clones possessing an ~170 bp EcoRI-BamHI fragment was grown in large volume and its plasmid purified. This plasmid contained the complete yeast invertase signal coding sequence fused to the left half of IGF-1 and was called P.I. IGF-1 L.H. RI-BamHI.

The desired ~170 bp EcoRI-BamHI fragment was isolated from this plasmid by digestion of the plasmid with EcoRI and BamHI in the appropriate buffers followed by slab gel fractionation of the reaction mix. Using standard techniques, the ~170 bp band of DNA was prepared for ligation. To complete the construction, the right half of IGF-1 was isolated as an ~120 bp BamHI-EcoRI fragment from the plasmid P.I. IGF-1 EcoRI-EcoRI-P.I. Promoter by digestion with EcoRI and BamHI in the appropriate buffers followed by elution from a gel slice after polyacrylamide slab gel fractionation of the digestion mixture. These two fragments, the ~170 bp EcoRI-BamHI and the ~120 bp BamHI-EcoRI, were ligated together in vitro under standard ligation conditions, with both fragments present in roughly equimolar concentrations. This ligation mixture was then terminated by the addition of EDTA to ~15 mM followed by phenol extraction, chloroform extraction 2×, and ethanol precipitation. The DNA pellet was then taken up in 1×EcoRI buffer and digested with EcoRI. The digest was then run on a 6 percent polyacrylamide slab gel and the DNA band staining at ~290 bp (as opposed to ~340 bp and 240 bp) was excised and prepared for ligation using standard techniques. This ~290 bp EcoRI-EcoRI fragment contained the entire yeast invertase signal coding sequence fused to the complete IGF-1 coding sequence.

Figure 13:
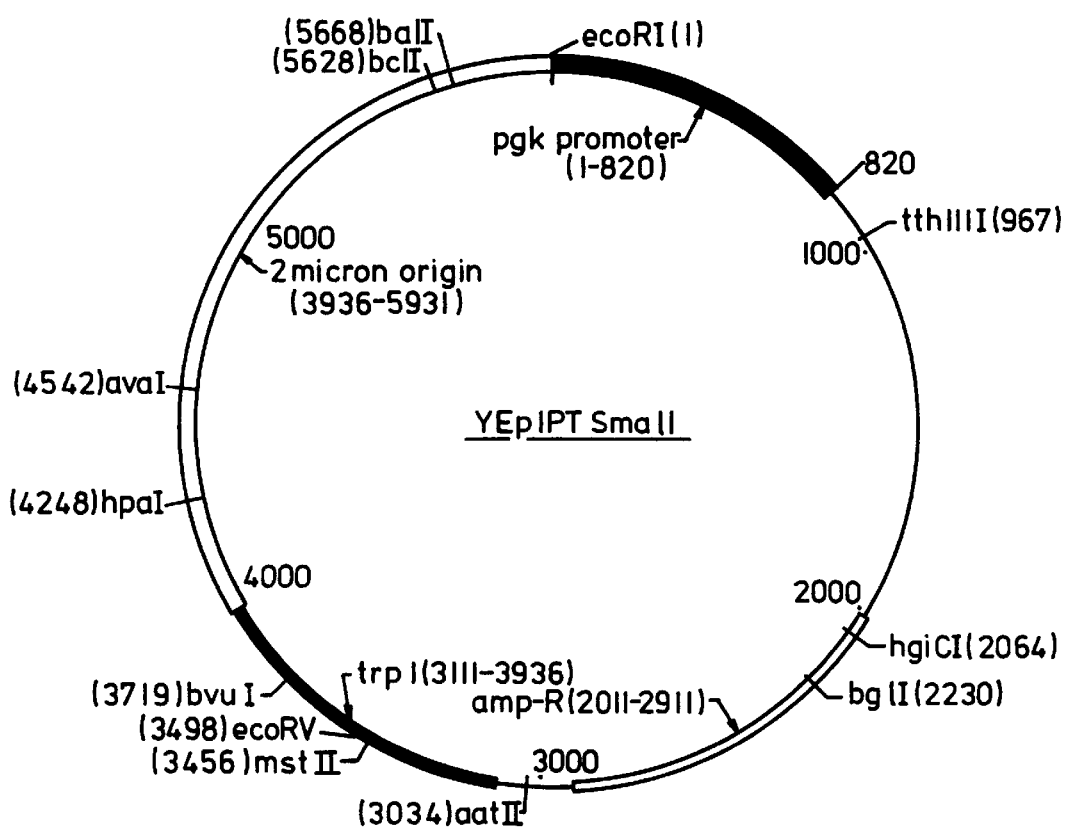
FIG. 13 shows the parental plasmid containing the yeast PGK promotor.

To express this protein, it was necessary to select a yeast vector with a promoter. The PGK promoter of the plasmid YEp1PT Small (see FIG. 13) was used. YEp1PT Small was constructed as a derivative of YEp1PT (21) by ClaI and PvuII digestion of YEp1PT in the appropriate buffers. The ClaI 5' protruding end was converted to a blunt end by use of DNA polymerase I (Klenow) under conditions recommended by the vendor. After blunting the (ClaI protruding ends, the blunt ends ClaI and PvuII) of the linearized vector were fused using T4 DNA ligase under standard ligation conditions. The resultant YEp1PT small vector was ~5.9 kbp in size (or ~2.7 kbp smaller than YEp1PT). Just as YEp1PT, YEp1PT small possesses the 2 micron origin and terminator, the PGK promoter, the TRP1 gene, and sequences from pBR322, including the β-lactamase gene.

YEp1PT Small was employed as a vector by insertion of the ~290 bp EcoRI fragment into the unique EcoRI site of the plasmid. EcoRI linearized YEp1PT Small vector was prepared by EcoRI digestion of YEp1PT Small followed by bacterial alkaline phosphatase (BAP) treatment (to prevent religation of the complementary termini). The BAP was removed by phenol extraction 3×, chloroform extraction 2×, and ethanol precipitation. Under standard ligation conditions, the ~290 bp EcoRI fragment was ligated into the vector.

Figure 14:
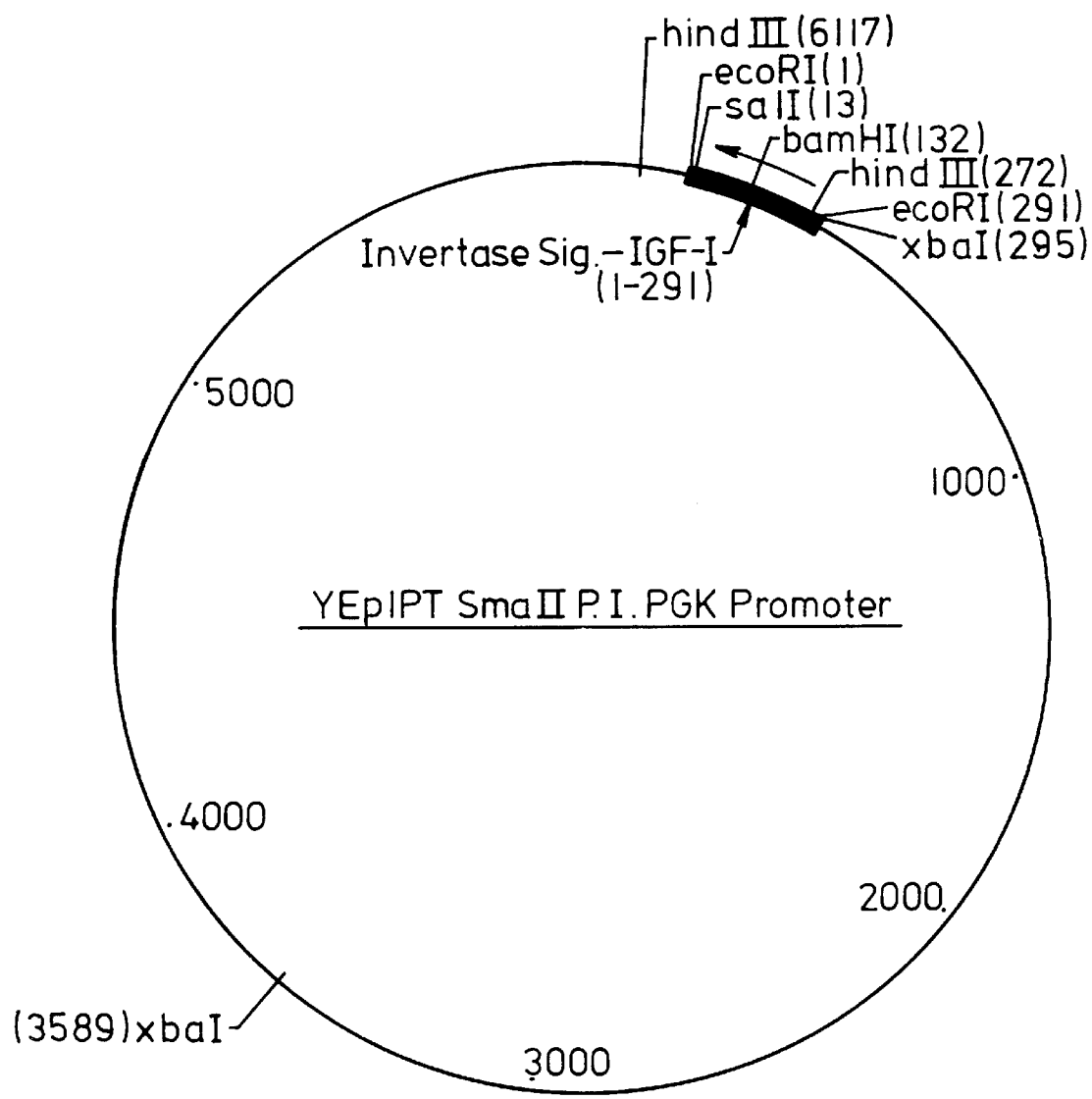
FIG. 14 depicts a yeast expression vector containing PGK promotor, invertase signal and human IGF-I gene.
Figure 20A:
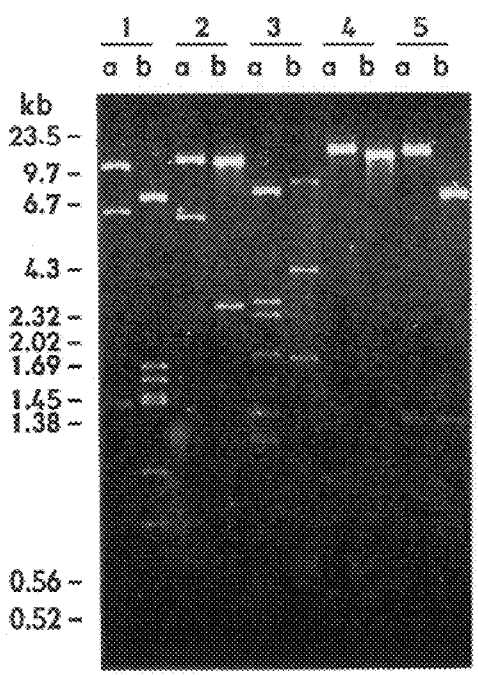
FIGS. 20A and 20B illustrate the results of electrophoresis of DNA fragments obtained using the probes of FIG. 19.
Figure 20B:
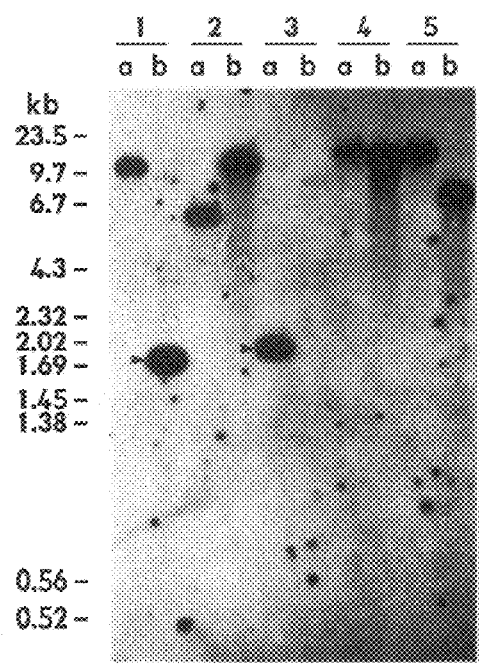

Competent *E. coli* 294 prepared according to Dagert and Ehrlich (3) were used as transformation hosts and the transformed culture was plated onto LB-Amp-Agar plates. Several transformants were miniscreened by the Birnboim and Doly procedure (4) and miniscreen plasmid DNAs were digested with HindIII in the appropriate buffer to determine the orientation of the insert. One of several transformants possessing a plasmid with a ~400 bp HindIII fragment was grown in large scale and its plasmid was purified. This plasmid was called YEp1PT Small P.I. IGF-1 PGK promoter (see FIG. 14) and was used to transform competent yeast strain 20B-12 (ATCC 20626) (αtrp pep4) cells employing the Hitzeman modification (19) of Hinnen et al. (17), and Beggs et al. (18) procedures.

Several yeast transformants were grown in suspension in identical fashion as were those of the P.I. IGF-1 EcoRI-EcoRI P.I. promoter plasmid transformation and supernates were measured for activity determined by a radioimmune assay method of Furlanetto et al. (23) as modified by Hintz et al. (24). Shake flask supernates of three transformants contained activities ranging from 38 to 53 ng/ml of supernate. Similarly, one of these transformants was selected and grown in larger scale, utilizing a 10 liter fermenter and the secreted IGF-1 activity in the supernate reached a peak of ~780 ng/ml. This fermentation supernate was also subjected to a radioreceptor assay (26) and was demonstrated to contain IGF-1 activity.

Stature Human IGF Production

To construct a DNA sequence coding for the α-factor pre-pro protein fused to the DNA sequence coding for mature IGF-I, an M-13 in vitro mutagenesis technique was employed. (See Regin et al., *Proc. Acad. Science (USA)* 75, 4208; Hutchinson, et al., *Journal Biological Chem.* 253, 6551; Gilliam, et al., Gene 8, 81 and 99; Gillam, et al., *Nucleic Acids Research* 6, 2973; Adelman, et al., DNA (June, 1983).)

To construct the M-13 plasmid, the plasmid YEp9T α-factor EcoRI-EcoRI IGF-I (FIG. 16) was digested with BglII and SalI and the ca. 1.5 Kbp fragment containing the α-factor promotor-signal fused to IGF-I was isolated by polyacrylamide gel electrophoresis. This fragment was then ligated under standard ligation conditions to an MP-8 (BRL) vector digested with B3BamH1 and SalI, and treated with bacterial alkaline phosphatase. This ligation mix was then transformed into competent JM4101 cells prepared according to the method of Dagert and Ehrlich (3). These transformants were then mixed with non-competent JM101 cells grown to log phase, mixed with top agar and plated onto LB agar plates. Several clear plaques Were picked and sequenced using the M-13 dideoxy sequencing technique to confirm the presence of an insertion into the Sal1-BamH1 sites of the vector.

To perform the deletion according to the method above, a single strand of DNA of the sequence

5' AGAGTTTCCGGACCT CTT TTATCCAAAG 3' was chemically synthesized by standard methods (2) and used to delete the DNA sequence

```
5' GAGGCTGAAGCTCTAGAATTCCCTGCC 3'
3' CTCCGACTTCGAGATCTTAAGGGACGG 5'
``` just preceding the IGF-1 coding sequence of the α-factor promotor/signal IGF-I fusion sequence. This construction was then isolated as a replicative form, using a large scale plasmid preparation procedure from a JM101 cell culture inoculated with this plasmid containing the deletion.

The isolated replicative form (10 mg) Was then digested with SalI, phenol-chloroform extracted and then ethanol precipitated and prepared for ligation. To this replicative form was ligated Sal I-EcoRI linkers. After ligation and inactivation of the ligase by phenol, chloroform extraction followed by ethanol precipitation, the material was digested with ~50 U EcoRI enzyme under standard conditions and then run onto a 6 percent polyacrylamide gel. The ca. 1.5 kbp RI-EcoRI fragment released was isolated from the gel and prepared for ligation using standard conditions.

Yeast vector was prepared by digestion of 10 mg YEP9T plasmid with 50 units of EcoRI followed by treatment with bacterial alkaline phosphatase. The digestion was then repeatedly phenol-chloroform extracted and then ethanol precipitated and prepared for ligation.

The ca. 1.5 kbp EcoRI-EcoRI fragment containing the deletion was then ligated to the EcoRI-EcoRI YEP9T vector and the ligation mix was then transferred into competent 294 cells prepared according to the method of Dagert and Erhlich (3) and miniscreened using the method of Birnboin and Doly (4). DNA prepared was screened by digestion with EcoRI and those DNAs illustrating an insertion of the ca. 1.5 kbp fragment were used to transform competent yeast strain 20B-12 (ATCC 2026) according to the modification of Hitzeman (19) of the Hinner, et al., (17), and Beggs, et al., (18) procedures.

Transformants were then grown in shaker flasks and supernates assayed and shown to have IGF-I activity by the radioimmune assay procedure of Furlanetto, et al., (23) as modified by Hintz, et al., (24).

One of these clones was grown in large scale in a 10-liter fermentor and IGF-I purified from the supernatant of this fermentation. This material was then subjected to amino terminal protein sequencing and shown to be mature IGF-I protein.

Human EGF is prepared in accordance with the invention following analogous procedures as those described above.

Construction, Expression, and Secretion of Human EGF

In a fashion similar to IGF-1, double stranded DNA (FIG. 15) synthesized either by chemical means or through polymerization reactions was assembled to form a mature EGF coding sequence, with a codon coding for methionine (ATG) just preceding the amino-terminal asparagine found in the mature protein, and a codon (GTC) substituting valine for methionine at residue number 21 from the amino-terminal asparagine. This construction was then attached at the 5' end to an additional coding sequence, which when expressed in yeast or bacteria produced a fusion protein. This fusion protein was then susceptible to CNBr cleavage at the methionine to release the valine substituted human EGF molecule.

To secrete the mature form of EGF from yeast, the above sequence coding for the mature protein was attached to the α-factor promoter/prepro sequence, the codon coding for valine at residue number 21 was replaced by ATG, and the appropriate deletion was made to bring the coding sequence for mature EGF adjacent to the α-factor signal coding sequence (FIG. 16). This construction was then inserted into the yeast vector Yep9T and transformed into yeast. Transformants produced as such expressed and secreted mature human EGF. In addition, the sequence coding for mature EGF was attached to the preinvertase signal sequence (FIG. 17) and this construction, when inserted into the yeast vector Yep1PT Small containing the PGK promoter, and transformed into yeast, resulted in the expression and secretion of human EGF.

Construction, Expression, and Secretion of Human IGF-II

A double stranded DNA sequence coding for mature IGF-II was constructed from a combination of synthetic and natural DNA sequences (FIG. 18). This coding sequence, which did not contain an internal methionine, was attached to the TrpE leader protein coding sequence and was expressed as a fusion protein. Mature IGF-II was chemically cleaved from the purified fusion product by the action of CNBr upon a methionine residue preceding the first residue (alanine) of the mature protein.

The IGF-II coding sequence was also attached to the α-factor promoter/prepro sequence and after the appropriate deletion was made to bring the 3' end of the α-factor signal coding sequence adjacent to the 5' end of mature IGF-II coding sequence, the construction was inserted into the Yep9T vector and transformed into yeast. Resultant transformants expressed and secreted mature human IGF-II. In the same manner, the sequence coding for mature IGF-II was attached to the preinvertase coding sequence. The resultant construction was inserted into Yep1PT Small and transformed into yeast. Transformants produced as such expressed and secreted mature human IGF-II.

Pharmaceutical Compositions

The compounds of the present invention can be formulated according to known methods to prepare pharmaceutically useful compositions, whereby the human IGF and human EGF or products hereof are combined in admixture with a pharmaceutically acceptable carrier vehicle. Suitable vehicles and their formulation, inclusive of other human proteins, e.g. human serum albumin are described, for example, in *Remington's Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective administration.

Notwithstanding that reference has been made to particular preferred embodiments of the present invention, it will be understood that the present invention is not to be construed as limited to such but rather to the lawful scope of the appended claims.

Bibliography

A. Rinderknecht, E. W. et al., *Proceedings National Academy of Sciences (USA)* 73, 2365 (1976).
B. Rinderknecht, et al., *Proceedings National Academy of Sciences (USA)* 73, 4379 (1976).
C. Blundell, et al., *Proceedings National Academy of Sciences (USA)* 75, 1980 (1978).
D. Rinderknecht, et al., *Journal of Biological Chemistry* 253, 2769 (1978), 2365 (1976).
E. Rinderknecht, et al., *FEBS Letters* 89, 283 (1978).
F. Zaph, et al., *Metabolism* 27, 1803 (1978).
G. Hintz, et al., *Journal of Clinical Endocrinology and Metabolism* 50, 405 (1980).
H. Blundell, et al., *Nature* 287, 781 (1980).
I. Hintz, et al., *Journal of Clinical Endo. and Metabolism* 51, 672 (1980).
J. Baxter, et al., *Journal of Clinical Endo. and Metabolism* 54, 474 (1980).
K. Hintz, et al., *Journal of Clinical Endo. and Metabolism* 54, 442 (1982).
L. Schoenle, et al., *Nature* 296, 252 (1982).
M. British Patent Application Publication No. 2007676A.
N. Wetzel, *American Scientist* 68, 664 (1980).
O. *Microbiology*, Second Edition, Harper and Row Publications Inc., Hagerstown, Md. (1973), especially pages 1122 et sequence.
P. *Scientific American* 245, 106 (1981).
1. Rinderknecht, E. and Humbel, R. E., *J. Biol. Chem.* 253, 8, 2769–2776 (1978).
2. Crea, R. and Horn, T., *Nucleic Acids Research* 8, 2331–2348 (1980).
3. Dagert, M. and Ehrlich, S. D., *Gene* 6, 23–28 (1979).
4. Birnboim, H. C. and Doly, J., *Nucleic Acids Research* 7, 1513–1523 (1979).
5. Maxam, A. and Gilbert, W., *Methods in Enzymology* 65, 499 (1980).
6. Villa-Komaroff et al., *Proc. Natl. Acad. Sci. USA* 75, 3727 (1979).
7. Rowenkamp and Firtel, *Dictyostelium Dev. Biol.* 79, 409 (1980).
8. Wunsch, E. et al., *Hoppe-Seyler's Z. Physiol. Chem. Bd.* 362, S1285–1287 (September 1981).
9. Maniatis, T. et al., *Molecular Cloning*, 426 (1982).
10. Kleid, D. G., *New York Acad. of Sci., Annals.* (in press)
11. Seifter, S. and Gallop, P. M., *The Proteins*, 2nd Ed. (H. Neurath, ed.) Vol. V, p. 659 (1966).
12. Nordwig, A., *Leder* 13, 10 (1962).
13. Lin, N. (U.S. Ser. No. 06/452,363, filed Dec. 22, 1982).
14. Laemmli, U. K. *Nature (London)* 227, 680–685 (1970).
15. Bolivar, F. et al., *Gene* 2, 95 (1977).
16. Chang, C. N. (U.S. Ser. No. 06/488337, filed Apr. 25, 1983 filed as a continuation U.S. Ser. No. 07/541,186 on Jun. 20, 1990, and issued as U.S. Pat. No. 5,010,003).
17. Hinnen, A. et al., *Proc. Natl. Acad. Sci. USA* 75, 1929–1933 (1978).
18. Beggs, J. D., *Nature* 275, 104–109 (1978).
19. Hitzeman, R. A. et al. U.S. Ser. No. 438,236, filed Nov, 1, 1982
20. Capon, D. (refer to Bovine Interferon patent number) (1983).
21. Hitzeman, R. A. et al., *Science* 219, 620–625 (1983).
22. Singh, A. (U.S. Ser. No. 06/488323, filed Apr. 25, 1983).
23. Furlanetto, R. W., Underwood, L. E., Van Wyk, J. J., D'Ercole, A. J., *J. Clin. Invest.* 60, 648 (1977).
24. Hintz, R. L., Liu, F., Marshall, L. B., Chung, D., *J. Clin. Endocrinol. Metab.* 50, 405 (1980).
25. Hitzeman, R. A. et al., *Proceedings of the Berkeley Workshop on Recent Advances in Yeast Molecular Biology: Recombinant DNA*. U.C. Press, Berkeley, p. 173 (1982).
26. Horner, J. M., Liu, F., Hintz, R. A., *J. Clin. Endocrinol. Metab.* 47, 6, p. 1287 (1978).
27. Rossi, J. J., Zierzek, R., Huang, T., Walker, P. A., Itakura, K., *J. Biol. Chem.* 257, 16, 9226 (1982).

What is claimed is:

1. A fusion protein comprising the amino acid sequence of mature human IGF-I as shown in FIG. 12 or a natural allelic variant thereof and, at the N-terminus of the mature IGF-I, a bacterial protein followed by an enzymatic proteolysis site linking the bacterial protein and the mature IGF-I.

* * * * *

UNITED STATES PATENT AND TRADEMARK OFFICE
CERTIFICATE OF CORRECTION

PATENT NO.    : 6,331,609 B1
DATED         : December 18, 2001
INVENTOR(S)   : Lee et al.

Page 1 of 1

It is certified that error appears in the above-identified patent and that said Letters Patent is hereby corrected as shown below:

<u>Column 26,</u>
Line 46, after IGF-I insert -- or natural allelic variant thereof --.

Signed and Sealed this

Seventeenth Day of June, 2003

JAMES E. ROGAN
*Director of the United States Patent and Trademark Office*